United States Patent
Babin

(10) Patent No.: US 9,372,150 B2
(45) Date of Patent: Jun. 21, 2016

(54) OPTICAL METHOD AND SYSTEM FOR MEASURING AN ENVIRONMENTAL PARAMETER

(71) Applicant: INSTITUT NATIONAL D'OPTIQUE, Québec (CA)

(72) Inventor: François Babin, Québec (CA)

(73) Assignee: INSTITUT NATIONAL D'OPTIQUE, Quebec (CA)

( * ) Notice: Subject to any disclaimer, the term of this patent is extended or adjusted under 35 U.S.C. 154(b) by 0 days.

(21) Appl. No.: 15/005,375

(22) Filed: Jan. 25, 2016

(65) Prior Publication Data
US 2016/0139036 A1    May 19, 2016

Related U.S. Application Data

(63) Continuation-in-part of application No. 14/449,511, filed on Aug. 1, 2014, now Pat. No. 9,244,002.

(51) Int. Cl.
| | |
|---|---|
| *G01N 21/00* | (2006.01) |
| *G01N 21/25* | (2006.01) |
| *G01N 21/27* | (2006.01) |

(52) U.S. Cl.
CPC ............. *G01N 21/255* (2013.01); *G01N 21/27* (2013.01); *G01N 2201/082* (2013.01); *G01N 2201/0833* (2013.01)

(58) Field of Classification Search
CPC ............. G02B 6/02304; G02B 6/2861; G02B 21/0032; G02B 21/0076; G02B 1/12; G02B 26/06; G02B 5/18; G02B 17/023; G02B 2006/1213; G02B 2006/1215; G02B 5/10; G02B 5/122; G02B 6/02266; G02B 6/02357
See application file for complete search history.

(56) References Cited

U.S. PATENT DOCUMENTS

| | | |
|---|---|---|
| 5,148,303 A | 9/1992 | Biard |
| 5,589,937 A | 12/1996 | Brininstool |
| 2002/0063866 A1 | 5/2002 | Kersey et al. |

(Continued)

FOREIGN PATENT DOCUMENTS

EP      0306227 B1    2/1992

OTHER PUBLICATIONS

B. J.-C. Deboux et al., A robust and miniature optical fibre pH sensor based on methylene blue dye adsorption, Proceeding of the SPIE, 1995, pp. 167-176, vol. 2542, Liverpool John Moores University, Liverpool, United Kingdom.

(Continued)

*Primary Examiner* — Michael P Stafira
(74) *Attorney, Agent, or Firm* — Fasken Martineau Dumoulin LLP

(57) ABSTRACT

An optical system for sensing an environmental parameter, comprising: an optical pulse generator for generating an excitation pulse; a pulse splitter for splitting the excitation pulse into a sensing pulse and a reference pulse; a sensing arm for receiving the sensing pulse, the sensing arm comprising an emission sensor for sensing the environmental parameter, the optical emission sensor generating a first measurement pulse having a measurement wavelength; a reference arm for receiving the reference pulse, the reference arm comprising an emission artifact adapted to convert the reference pulse into a second measurement pulse having the measurement wavelength; a time delay line for delaying a relative propagation of the measurement pulses; a light detector for measuring an optical energy of the first and second measurement pulses; and an optical link for optically connecting the pulse generator to the pulse splitter, and the sensing and reference arms to the light detector.

20 Claims, 8 Drawing Sheets

(56) References Cited

U.S. PATENT DOCUMENTS

| | | | |
|---|---|---|---|
| 2007/0064945 A1* | 3/2007 | Yuan | H04L 9/0858 380/263 |
| 2012/0147381 A1 | 6/2012 | Leblanc et al. | |
| 2012/0315033 A1* | 12/2012 | Sugiya | H04B 10/07 398/34 |
| 2013/0062508 A1 | 3/2013 | Kanter et al. | |

OTHER PUBLICATIONS

K. T. V. Grattan et al., Dual Wavelength Optical Fibre Sensor for pH Measurement, Biosensors, 1987/1988, p. 17-25, vol. 3, School of Electrical Engineering and Applied Physics, London, United Kingdom.

* cited by examiner

OPTICAL METHOD AND SYSTEM FOR MEASURING AN ENVIRONMENTAL PARAMETER

TECHNICAL FIELD

The present invention relates to the field of optical measurement methods and systems, and more particularly to optical methods and systems using an emission sensor.

BACKGROUND

In various industries, point sensors are installed at various intervals along optical fibers that span long distances, e.g. from hundreds of meters to tens of kilometers. One type of sensor measures environmental parameters through the change in the spectral optical loss of the sensor. These sensors usually work at a number of different wavelengths, often tens to one or two hundred nanometers apart. Spectral losses, i.e. optical losses that vary with wavelength, and spectral loss stability in the fiber link then become important factors. In order to measure spectral loss in point sensors installed along optical fibers, often of great lengths, time evolution techniques such as fluorescence lifetime technique or ring down spectroscopy are usually used. These techniques can be time-consuming or require low-dispersion fibers which are inadequate in coupling thereto several sensors.

Therefore, there is a need for an improved optical sensing method and system.

SUMMARY

According to a first broad aspect, there is provided an optical system for sensing an environmental parameter of a sample, comprising: an optical pulse generator for generating an excitation pulse having an excitation wavelength; a pulse splitter for splitting the excitation pulse into a sensing pulse and a reference pulse; a sensing arm connected to the pulse splitter for receiving the sensing pulse therefrom, the sensing arm comprising an optical emission sensor for sensing the environmental parameter of the sample, the optical emission sensor generating at least one first measurement pulse, each first measurement pulse having a respective measurement wavelength different from the excitation wavelength; a reference arm connected to the pulse splitter for receiving the reference pulse therefrom, the reference arm comprising an emission artefact adapted to convert the reference pulse into a at least one second measurement pulse each having the respective measurement wavelength; a time delay line contained in one of the sensing arm and the reference arm, the time delay line for delaying a propagation of one of the at least one first measurement pulse and the at least one second measurement pulse relative to a propagation of another one of the at least one first measurement pulse and the at least one second measurement pulse; a light detector for detecting the at least one first measurement pulse and the at least one second measurement pulse and measuring an optical energy of the at least one first measurement pulse and the at least one second measurement pulse; and at least one optical link for optically connecting the pulse generator to the pulse splitter, and the sensing and reference arms to the light detector.

In one embodiment, the at least one optical link comprises a single optical link, the at least one first measurement pulse and the at least one second measurement pulse corresponding to back-scattered light emitted by the emission sensor and the emission artefact, respectively.

In another embodiment, the at least one optical link comprises a first optical link for optically connecting the pulse generator to the pulse splitter, and a second optical link for optically connecting the sensing and reference arms to the light detector.

In one embodiment, the at least one first measurement pulse and the at least one second measurement pulse correspond to back-scattered light emitted by the emission sensor and the emission artefact, respectively.

In another embodiment, the at least one first measurement pulse and the at least one second measurement pulse correspond to forward-scattered light emitted by the emission sensor and the emission artefact, respectively.

In accordance with a second broad aspect, there is provided a method for remotely sensing an environmental parameter, comprising: generating an excitation pulse having an excitation wavelength; propagating the excitation pulse along at least one optical link; splitting the excitation pulse into a sensing pulse and a reference pulse; propagating the sensing pulse in a sensing arm, the sensing arm comprising an emission sensor, thereby sensing the environmental parameter and generating at least one first measurement pulse, each first measurement pulse having a respective measurement wavelength different from the excitation wavelength; propagating the reference pulse in a reference arm, the sensing arm comprising an emission artefact, thereby generating at least one second measurement pulse, each second measurement pulse having the respective measurement wavelength; delaying a propagation of one of the at least one first measurement pulse and the at least one second measurement pulse relative to a propagation of another one of the at least one first measurement pulse and the at least one second measurement pulse; propagating the at least one first measurement pulse and the at least one second measurement pulse in the at least one optical link; and measuring an optical energy of the at least one first measurement pulse and the at least one second measurement pulse.

In one embodiment, the step of propagating the excitation pulse along at least one optical link comprises propagating the excitation pulse along a single optical link, and said propagating the at least one first measurement pulse and the at least one second measurement pulse in the at least one optical link comprises propagating the at least one first measurement pulse and the at least one second measurement pulse along the single optical link, the at least one first measurement pulse and the at least one second measurement pulse corresponding to back-scattered light emitted by the emission sensor and the emission artefact, respectively.

In another embodiment, the step of propagating the excitation pulse along at least one optical link comprises propagating the excitation pulse along a first optical link, and said propagating the at least one first measurement pulse and the at least one second measurement pulse in the at least one optical link comprises propagating the at least one first measurement pulse and the at least one second measurement pulse along the second optical link different from the first optical link.

In one embodiment, the at least one first measurement pulse and the at least one second measurement pulse correspond to back-scattered light emitted by the emission sensor and the emission artefact, respectively.

In another embodiment, the at least one first measurement pulse and the at least one second measurement pulse correspond to forward-scattered light emitted by the emission sensor and the emission artefact, respectively.

In accordance with another broad aspect, there is provided an optical system for sensing an environmental parameter of a sample, comprising: an optical pulse generator for generating an excitation pulse having an excitation wavelength and at least one reference pulse, each one of the at least one reference pulse having a respective measurement wavelength different from the excitation wavelength; a sensing arm optically connected to the optical pulse generator for receiving at least a portion of the excitation pulse therefrom, the sensing arm comprising an optical emission sensor for sensing the environmental parameter; the optical emission sensor generating at least one measurement pulse each having the respective measurement wavelength; a reference arm optically connected to the optical pulse generator for receiving the at least one reference pulse therefrom; a time delay line contained in one of the sensing arm and the reference arm, the time delay line for delaying a propagation of one of the at least one measurement pulse and the at least one a reference pulse relative to a propagation of another one of the at least one measurement pulse and the at least one reference pulse; a light detector for detecting the at least one measurement pulse and the at least one reference pulse and measuring an optical energy of the measurement pulse and the reference pulse; and an optical link for optically connecting the pulse generator to the sensing and reference arms, and the sensing and reference arms to the light detector.

In one embodiment, the optical system further comprises a beam splitter optically connected to the optical link and the sensing and reference arms for propagating the excitation pulse into the sensing arm and the at least one reference pulse into the reference arm.

In one embodiment, the reference arm comprises an optical reflector adapted to reflect the at least one reference pulse.

In another embodiment, the reference arm comprises an optical loop.

In another embodiment, the optical system further comprises an optical coupler optically connected to the optical link and the sensing and reference arms for propagating at least a portion of the excitation pulse into the sensing arm and at least a portion of the at least one reference pulse into the reference arm.

In accordance with a further broad aspect, there is provided a method for remotely sensing an environmental parameter, comprising: generating an excitation pulse having an excitation wavelength and at least one reference pulse, each one of the at least one reference pulse having a respective measurement wavelength different from the excitation wavelength; propagating the excitation pulse and the at least one reference pulse along an optical link; propagating the excitation pulse in a sensing arm, the sensing arm comprising an emission sensor, thereby sensing the environmental parameter and generating at least one measurement pulse each having the respective measurement wavelength; propagating the at least one reference pulse in a reference arm; delaying a propagation of one of the at least one measurement pulse and the at least one measurement pulse relative to a propagation of another one of the at least one measurement pulse and the at least one measurement pulse; propagating the at least one measurement pulse and the at least one measurement pulse in the optical link; and measuring an optical energy of the at least one measurement pulse and the at least one reference pulse.

In one embodiment, the method further comprises propagating the excitation pulse and the at least one reference pulse into a beam splitter optically connected to the optical link and the sensing and reference arms, thereby propagating the excitation pulse into the sensing arm and the at least one reference pulse into the reference arm.

In one embodiment, the step of propagating the at least one reference pulse in a reference arm comprises reflecting the at least one reference pulse.

In another embodiment, the step of propagating the at least one reference pulse in a reference arm comprises propagating the at least one reference pulse in an optical loop.

In one embodiment, the method further comprises propagating the excitation pulse and the at least one reference pulse into an optical coupler connected to the optical link and the sensing and reference arms, thereby propagating at least a portion of the excitation pulse into the sensing arm and at least a portion of the at least one reference pulse into the reference arm.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Figure 1:
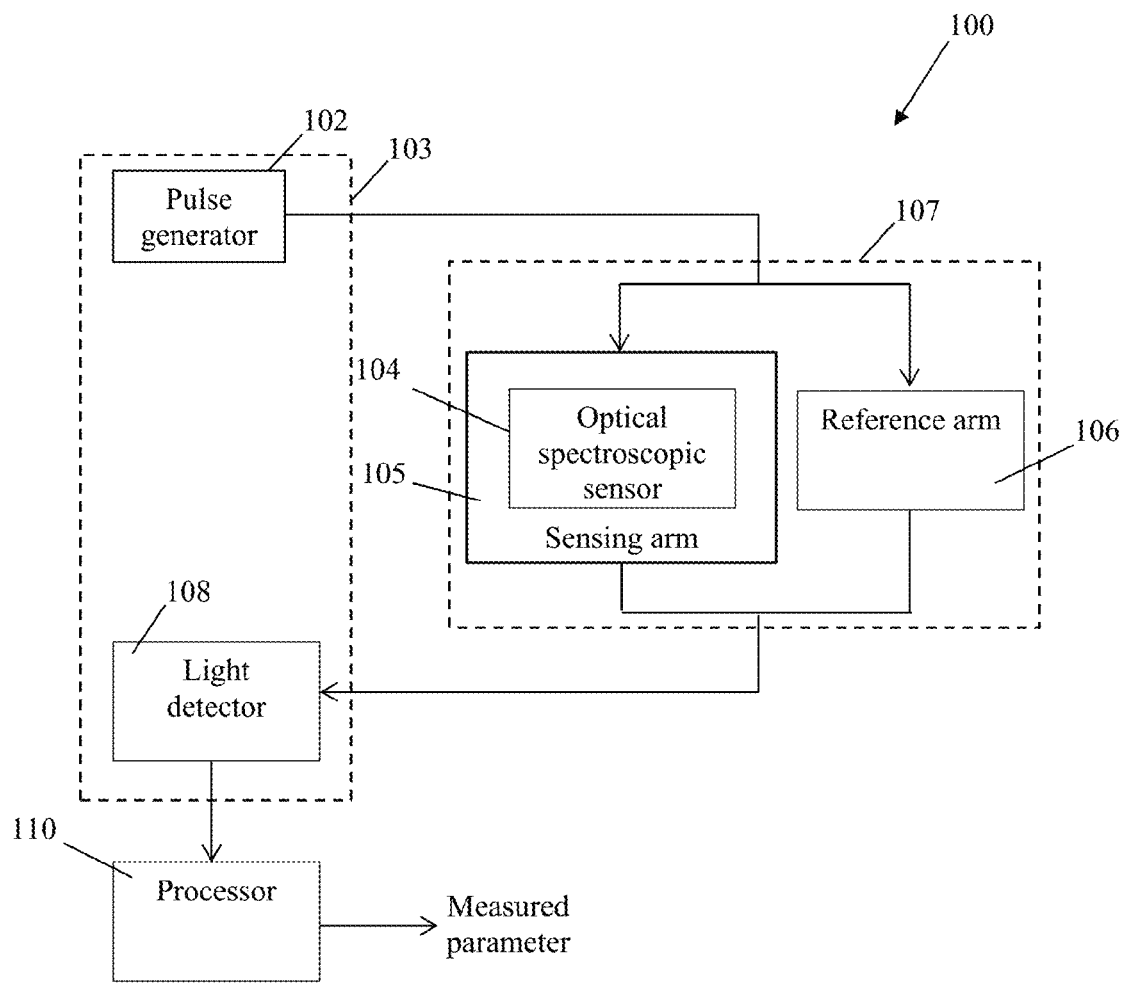
FIG. 1 is a block diagram of an optical system for measuring an environmental parameter, in accordance with an embodiment.

FIG. 1 illustrates one embodiment of an optical system 100 for remotely measuring an environmental parameter. The environmental parameter may be a physical characteristic of a fluid such as a gas or a liquid, a physical characteristic of a solid, etc. The optical system 100 comprises an optical pulse generator 102, a spectral loss ratiometric sensor 104 (hereinafter referred to as a spectro-ratiometric sensor), a sensing arm 105 comprising the spectro-ratiometric sensor 104, a reference arm 106, a light detector 108, and a processor 110. The pulse generator 102 and the light detector 108 form together an interrogator unit 103. The sensing arm 105 comprising the spectro-ratiometric sensor 104 and the reference arm 106 form together a sensing unit 107.

The pulse generator 102 is adapted to emit at least two optical pulses each having a different wavelength. While in the description below it is referred to two light pulses having different wavelengths, it should be understood that the pulse generator 102 may be adapted to generate more than two pulses having different wavelengths.

In one embodiment, the at least two pulses each have a different wavelength comprised in the infrared range such as in the telecommunication bandwidth.

In another embodiment, the at least two pulses each have a different wavelength comprised in the ultraviolet (UV) range, the visible (VIS) range or the near-infrared (NIR) range. The two light pulses may both have a different wavelength contained in the VIS range or the NIR range. In another example, one pulse may have a wavelength contained in the VIS range and the other pulse may have a wavelength contained in the NIR range.

In one embodiment, light contained in the VIS range has a wavelength comprised between about 390 nm and about 700 nm. In one embodiment, light contained in the NIR range has a wavelength comprised between about 700 nm and about 900 nm. In one embodiment, light contained in the UV range has a wavelength comprised between about 200 nm and about 390 nm.

The pulse generator 102 may be adapted to emit substantially concurrently at least two pulses of light each having a different wavelength. Alternatively, the pulse generator 102 may be adapted to successively emit at least two pulses of light each having a different wavelength.

In one embodiment, the pulse generator 102 comprises at least two different light sources each adapted to emit light pulses at a respective wavelength.

In one embodiment, the pulse generator 102 may comprise at least one pulsed light source such as a Q-switched laser. In another embodiment, the pulse generator 102 may comprise at least one light source and at least one optical modulator such as an electro-optic modulator for modulating the light emitted by the light source and generating the light pulses. The pulse generator 102 may also be a laser diode of which the current provided by a power supply is modulated for generating pulses.

The pulse generator 102 is optically connected to the sensing arm 105 which comprises the spectro-ratiometric sensor 104 and to the reference arm 106 so that the generated pulses having different wavelengths be each split into two pulses, i.e. a sensing pulse and a reference pulse for each wavelength. For each wavelength, the sensing pulse propagates through the spectro-ratiometric 104 along the sensing arm 105 while the reference pulse propagates along the reference arm 106. It should be understood that the system 100 comprises any adequate device (not shown) for splitting or dividing each light pulse emitted by the pulse generator 102 into two pulses, such as a beam or pulse splitter, a coupler, or the like. In one embodiment, the sensing pulse and the reference pulse are substantially identical. In this case, a 3 dB coupler may be used for splitting the generated pulse into substantially identical pulses. In another embodiment, the sensing pulse and the reference pulse may be different. For example, the sensing and reference pulses may have different amplitudes.

The spectro-ratiometric sensor 104 is an optical sensor of which the optical absorption spectrum, and/or the optical loss spectrum characteristics change as a function of the environmental factor/parameter to be measured, i.e. a factor or parameter of the environment surrounding the optical loss sensor 104. As a result, the differential loss experienced by at least two optical pulses having different wavelengths and propagating therethrough varies as a function of the environmental parameter value. In order to determine the value of the environmental parameter, the optical spectro-ratiometric sensor 104 requires the use of at least two different wavelengths, i.e. the optical loss at at least two different wavelengths must be known in order to determine the value of the environmental parameter. Therefore, the spectro-ratiometric sensor 104 may also be referred to as a differential loss sensor.

The spectro-ratiometric sensor 104 may be adapted to sense any adequate environmental factor/parameter such as a temperature, a strain, a pressure, an acoustic signal, a molecular concentration, an ion concentration, an acceleration, humidity, a magnetic and/or electric field, an electrical current, a biomarker, a radiation, or the like. As a result, when the value of the environmental parameter varies, the amount of loss experienced by the light pulses propagating through the optical spectro-ratiometric sensor 104 varies. In one embodiment, the optical loss characteristics (comprising absorption) for the optical loss sensor depend on the wavelength of the light pulse. As a result, when the environmental parameter has a given value, the loss of a first light pulse having a first wavelength and propagating through the spectro-ratiometric sensor 104 may be different from the loss experienced by a second pulse having a second and different wavelength. Similarly, when the environmental parameter experiences a given variation, the loss variation for a first light pulse having a first wavelength and propagating through the spectro-ratiometric sensor 104 may be different from the loss variation experienced by a second pulse having a second and different wavelength.

In one embodiment, the spectro-ratiometric sensor 104 uses a dye or a light-absorbing indicator as an indicator of change in the environmental parameter/factor. The light-absorbing indicator could be any adequate compound that changes its optical absorption spectrum under the influence of an environmental parameter/factor. For example, the light-absorbing indicator may comprise adequate quantum dots or polymer semiconductors.

In one embodiment, the spectro-ratiometric sensor 104 directly provides an optical response to a given environmental parameter or mix of parameters. In the case of a chemical spectro-ratiometric sensor, direct sensitivity refers to an indicator which is directly in equilibrium with the analyte, such as a pH sensor or optode.

In another embodiment, the spectro-ratiometric sensor 104 indirectly provides an optical response to a given environmental parameter or mix of parameters. In the case of a chemical spectro-ratiometric sensor, indirect sensitivity in a chemical sensor refers to a chemical equilibrium between the indicator and the analyte which is carried on by many intermediates which are in equilibrium with each other, such as an ion sensor.

In one embodiment, the spectro-ratiometric sensor 104 comprises an optical fiber-based optode which uses a sensing membrane deposited on an adequate substrate exterior to the fiber, on the fiber tip or surrounding the fiber core. When using a membrane as an optical fiber cladding for chemical spectro-ratiometric sensors 104, the analyte may diffuse into the membrane/cladding and a chemical indicator is provided in the cladding for causing a variation of the optical absorption as a function of the chemical species. The cladding is interrogated by the evanescent wave of the guided light in the optical fiber. Analysis of the measured absorption spectra provides an indication of the presence of given chemicals. When using the evanescent wave sensors for other environmental parameters/factors, the variation of the optical absorption of the cladding is function of the environmental parameter/factor. Physical principles that induce changes in an absorption or loss spectrum in a sensing cladding may comprise thermochromism for temperature sensing, solvatochromism for solvent vapor detection, electrochromism for current sensing, ionochromism for ion sensing, halochromism for pH sensing, piezochromism for pressure sensing, and/or the like.

In another embodiment, the spectro-ratiometric sensor 104 comprises an optical fiber-based optode which uses no membranes. In this case, the fiber core or tip is directly in contact with a solution for example.

In one embodiment, the spectro-ratiometric sensor 104 operates only in the UV, VIS and/or NIR range. In this case, the pulse generator 102 is adapted to generate pulses having different wavelengths comprised in the UV, VIS and/or NIR range.

In one embodiment, the reference arm 106 comprises an optical waveguide having a predetermined length. The predetermined length of the reference arm 106 is chosen so as to be different from the length of the sensing arm 105 which comprises the spectro-ratiometric sensor 104. The length difference between the sensing arm 105 and the reference arm 106 is chosen so that, for each wavelength, the sensing pulse and the reference pulse substantially do not overlap in time when reaching the light detector 108.

It should be understood that, for each wavelength, the sensing pulse may experience a different loss with respect to the reference pulse since it propagates through the spectro-ratiometric sensor 104 which induces the different loss according to the value of the sensed environmental parameter. Therefore, the different loss experienced by the sensing pulse relative to the reference pulse is indicative of the value of the environmental parameter, when combined with the loss experienced by the other wavelength pulse(s) relative to their reference pulse(s).

In one embodiment, the length of the sensing arm 105 is greater than that of the reference arm 106. In another embodiment, the length of the sensing arm 105 comprising the spectro-ratiometric sensor 104 is less than that of the reference arm 106.

In one embodiment, an optical delay line is inserted either in the sensing arm 105 or in the reference arm 106 to induce an additional time delay between the sensing pulse and the reference pulse. The optical delay line may be any adequate device adapted to induce a time delay. For example, the optical delay line may be a multipass cell. In another example, the optical delay line may be an optical waveguide such as an optical fiber having a given length chosen to induce an adequate time delay between the sensing pulse and the reference pulse so that they do not overlap in time while reaching the light detector 108.

The sensing arm 105 comprising the spectro-ratiometric sensor 104, and the reference arm 106 are optically connected to the light detector 108 via an optical link or connection so that, for each wavelength, the sensing pulse and the reference pulse may propagate up to the light detector 108. It should be understood that any adequate optical link adapted to propagate optical pulses having the wavelengths generated by the pulse generator 102 may be used. In one embodiment, the optical link is an optical fiber. The optical fiber may be single mode at the wavelengths of the light pulses generated by the pulse generator 102. Alternatively, the optical fiber may be multimode at the wavelengths of the light pulses generated by the pulse generator 102.

In one embodiment, the sensing arm 105 and the reference arm 106 are connected to the optical detector 108 via a same optical waveguide such as an optical fiber. In this case, the optical system 100 further comprises an adequate device for receiving the sensing pulses and the reference pulses from the sensing arm 105 and the reference arm 106, respectively, and propagating the received sensing and reference pulses into the same optical waveguide. For example, the optical system 100 may further comprise an optical beam or pulse combiner, an optical coupler, or the like to propagate the sensing and reference pulses in the same optical waveguide.

The light detector 108 is adapted to detect light having the same wavelengths as the ones of the light pulses emitted by the pulse generator 102, and measure the optical energy of the sensing and reference pulses for each wavelength. While in the present description it is said to be adapted to measure the optical energy of light pulses, it will be clear to those skilled in the art that the light detector 108 may be adapted to measure any physical quantity equivalent to an optical energy such as a number of photons, a pulse amplitude, and/or the like. In one embodiment, the light detector 108 is a photon counting detector. In an embodiment in which a time delay is introduced in the sensing arm 105, the reference pulse is the first pulse to reach the light detector 108. In this case, for each wavelength, the light detector 108 first detects the reference pulse and measures its optical energy. Then, the light detector 108 detects the sensing pulse and measures its respective optical energy. In an embodiment in which the time delay is introduced in the reference arm, the sensing pulse is the first pulse to reach the light detector 108. In this case, for each wavelength, the light detector 108 first detects the sensing pulse and measures its optical energy. Then, the light detector 108 detects the reference pulse and measures its respective optical energy.

The processor 110 is in communication with the light detector 108 in order to receive the measured optical energy for the sensing and reference pulses at each wavelength from the light detector 108. The processor 110 is adapted to determine the value of the sensed environmental parameter using the difference between the optical energy of the detected sensing pulse and that of the detected reference pulse for each wavelength. For each wavelength, the loss experienced by the sensing pulse while propagating in the spectro-ratiometric sensor 104 is determined using the optical energy of the sensing and reference pulses. In one embodiment, the loss experienced by the reference pulse or the sensing pulse in the optical delay line is neglected. In another embodiment, the loss experienced by the sensing pulse while propagating in the optical loss sensor 104 is obtained while further taking into account the optical loss experienced by the sensing pulse or the reference pulse while propagating in the optical delay line.

In one embodiment, once the optical system 100 has been assembled, the resulting assembly consisting of the reference arm, the sensing arm and/or any additional components such as a pulse combiner and a pulse splitter is calibrated by exposing the spectro-ratiometric sensor 104 to environments of known values of the environmental factor/parameter. For each environment of known value, the optical energies of the sensing and reference pulses are recorded for all of the at least two measurement wavelengths to be generated by the pulse generator. Other values may be recorded, such as the ratio of the sensing arm's pulse energy over the reference arm's pulse energy at all of the at least two measurement wavelengths and the like. In another embodiment and more generally, the pulse energy from the sensing arm 105 and the pulse energy from the reference arm 106 are measured and recorded at a number of wavelengths, not only the at least two wavelengths to be generated by the pulse generator 102 of the system 100, and are measured and recorded for all of the environments of known values of the environmental factor/parameter at the aforementioned number of wavelengths. This data is to become the input to an algorithm along with the recorded pulse energy from the sensing arm 105 and the recorded pulse energy from the reference arm 106 at all of the at least two wavelengths of the measurement system 100 to determine the value of the unknown environmental factor/parameter. In one embodiment, it may be preferable that the calibration hardware be the same as the measurement system to be deployed. In another embodiment, they may be different. The ensemble could also be calibrated before deployment with respect to temperature for example. The output from this calibration step could then also become an input to the measurement algorithm, or a look up table could then be used if the temperature is known somehow. In one embodiment, the assembly is designed to be independent of any parameter except, eventually, wavelength (which is known). The algorithms could, for example, take into account that in the sensing arm 105, there are other losses to account for besides the loss in the spectro-ratiometric sensor 104. There is, for example, coupling losses into and out of the spectro-ratiometric sensor 104. Losses occurring in the sensing arm 105 may also be considered. There could be other optical elements that generate coupling losses and/or propagation losses. All of these losses should have a linear relationship with the input pulse energy to the sensing arm 105. The loss due to absorption or otherwise in the spectro-ratiometric sensor 104 itself due to the environmental factor/parameter can be determined if the losses that are not due to the environmental factor/parameter are calibrated with respect to wavelength and other parameters or engineered to be independent of any other factor other than absorption/loss in the spectro-ratiometric sensor.

In one embodiment, the optical system 100 comprises at least one optical link or waveguide for optically connecting the pulse generator 102 to the sensing unit 107, and the sensing unit 107 to the light detector 108, the length of said optical link being such that the optical signal propagating from the generator 102 to the sensing unit 107 and then to the light detector 108 suffers high loss or high differential loss. The length of the optical connection is such that, for the wavelengths contained in the VIS range and/or the NIR range, the generated pulses that become the sensing and reference pulses experience high loss or high differential loss while propagating along the optical link. For example, the high loss or high differential loss optical connection may comprise at least one optical fiber having a given length presenting high loss for wavelengths comprised in the VIS range and/or NIR range. In one embodiment, high loss corresponds to a loss that would bring to detected signal within about 20 dB of the system's optical detection limit.

In one embodiment, the optical system 100 operates in transmission so that the sensing pulse at each wavelength makes only one pass through the spectro-ratiometric sensor 104. In one embodiment, a first optical waveguide optically connects the pulse generator 102 to the sensing unit 107, and a second and different optical waveguide optically connects the sensing unit 107 to the light detector 108. A first optical coupler may be used at the output of the first optical waveguide to split the incoming pulses generated by the pulse generator 102 into sensing pulses and reference pulses. A second optical coupler may be used for collecting the sensing pulses coming from the spectro-ratiometric sensor 104 and the reference pulses coming from the reference arm 106 and coupling them into the second optical waveguide. In another embodiment, a same optical waveguide optically connects both the pulse generator 102 and the light detector 108 on one end to the spectro-ratiometric sensor 104 and the reference arm 106 on the other end. In this case, a first circulator may be used for optically connecting together the pulse generator 102, the light detector 108, and the input of the single optical waveguide so that a pulse generated by the pulse generator 102 be propagated in the optical waveguide and a pulse coming from the optical waveguide be transmitted to the light detector 108. A second circulator may be used for optically connecting together the output of the optical waveguide, the sensing arm 105, and the reference arm 106. A first coupler may connect one output of the circulator to the sensing and reference arms 105 and 106 so that a pulse coming from the optical waveguide be split into a sensing pulse to be propagated in the sensing arm 105 and a reference pulse to be propagated into the reference arm 106. A second coupler may connect an input of the circulator to the outputs of the sensing and reference arms 105 and 106 so that the sensing pulse coming from the spectro-ratiometric sensor 104 and the reference pulse coming from the reference arm 106 be coupled into the optical waveguide.

In another embodiment, the optical system 100 operates in reflection. In this case, the sensing and reference arms 105 and 106 each comprise a light reflector at the end thereof for reflecting the sensing and reference pulses, respectively. It should be understood that any adequate light reflector adapted to reflect a light pulse may be used. For example, a straight cleaved fiber end coated with aluminum may be used. In one embodiment, a single and same optical waveguide optically connects the optical pulse generator 102 and the light detector 108 on one end to the sensing and reference arms 105 and 106 on the other end. As described above, a circulator may be used to optically connect together the pulse generator 102, the light detector 108, and the input of the generator 102, the light detector 108, and the input of the optical waveguide. A coupler optically connects together the output of the optical waveguide, the sensing arm 105 so that a pulse coming from the optical waveguide be split into the sensing pulse and the reference pulse, and the sensing and reference pulses reflected by the optical reflectors be combined into the optical waveguide.

In another embodiment, two different optical waveguides may be used for optically connecting the pulse generator 102, the light detector 108, the sensing arm 105, and the reference arm 106. A first end of a first optical waveguide is connected to the pulse generator 102 and the second end of the first optical waveguide is connected to a circulator. A first output of the circulator is connected to a coupler for splitting a pulse coming from the first optical waveguide into a sensing pulse to be propagated in the sensing arm 105 and a reference pulse to be propagated in the reference arm 105. The sensing and reference pulses are each reflected by their respective optical reflector and propagates back to the splitter/coupler and then to the circulator. The sensing and reference pulses exit the circulator by a second output which is optically connected to the second optical waveguide. The other end of the second optical waveguide is connected to the optical detector 108 so that the reflected sensing and reference pulses be detected by the light detector 108. In a further embodiment, the circulator may be omitted and a coupler may be used for connecting together the first and second optical waveguides and the sensing and reference arms 105 and 106.

In one embodiment, the light detector 108 comprises at least two photodetectors each adapted to detect light having a wavelength corresponding to that of a respective pulse generated by the pulse generator 102. In this case, the system may further comprise a wavelength-division multiplexing (WDM) coupler for coupling the sensing and reference pulses having a first wavelength to a first photodetector adapted to detect light having the first wavelength, and coupling the sensing and reference pulses having a second wavelength to a second photodetector adapted to detect light having the second wavelength. In another embodiment, a power divider coupler may be used to split each pulse coming from the sensing unit into two pulses. A respective bandpass filter is located at each output of the power divider coupler. The bandpass filter positioned between a first output of the power divider coupler and the photodetector adapted to detect light having the first wavelength is adapted to allow pulses having the first wavelength to propagate therethrough while preventing the propagation of pulses having the second wavelength. The bandpass filter positioned between the second output of the power divider coupler and the photodetector adapted to detect light having the second wavelength is adapted to allow pulses having the second wavelength to propagate therethrough while preventing the propagation of pulses having the first wavelength. The power divider coupler may be a 3 dB coupler for example.

In one embodiment, the light detector 108 comprises a photon counting detector adapted to measure photon numbers. In this case, the optical system 100 may comprise a controller operatively connected to the pulse generator 102 and the photon counting detector. The controller may be adapted to control the pulse generator 102 to trigger the generation of pulses and the photon counting detector. Knowing the time at which a pulse has been generated by the pulse generator 102, the controller may determine time windows during which the sensing pulse and the reference pulse will be received by the photon counting detector using the characteristics of the components of the optical system 100 such as the propagation time of the pulses, the time delay experienced by the sensing pulse or the reference pulse, etc. The controller may activate the photon counting detector only during the determined time windows.

The optical system 100 may be referred to as a differential optical loss sensing system since it uses at least two different wavelengths for measuring the value of an environmental parameter through the change in the absorption or loss spectrum of an optical loss sensor.

In one embodiment, the spectro-ratiometric sensor 104 is an ion or molecular concentration sensor that may come in the form of a fiber optic sensor of which the shape of the optical absorption spectrum or loss spectrum changes with the ion or molecular concentration in a fluid surrounding the fiber optic sensor. The optical loss of optical signals having at least two different wavelengths is measured in order to determine the change in the absorption/loss spectrum and subsequently the ion or molecular concentration.

In one embodiment and in order to transmit light over very great fiber lengths, light of wavelength in the range of 900 to 1900 nm is usually used, along with low-OH fibers. Particularly, the telecommunication band around 1550 nm is usually used. Interrogating a sensor at the end of a very long fiber link, such as tens of kilometers, is thus usually done in the low fiber loss spectral range, and particularly in the telecommunication band. On the other hand, some optical loss sensors only operate in the VIS or NIR range. These sensors are not considered in systems requiring long optical link(s) which therefore present(s) high optical loss, such as multiple kilometers of optical fiber, since measuring the loss in the sensing element of such a sensor is usually considered impractical or unreliable because of high loss and/or high differential loss in the fiber link(s).

Figure 2:
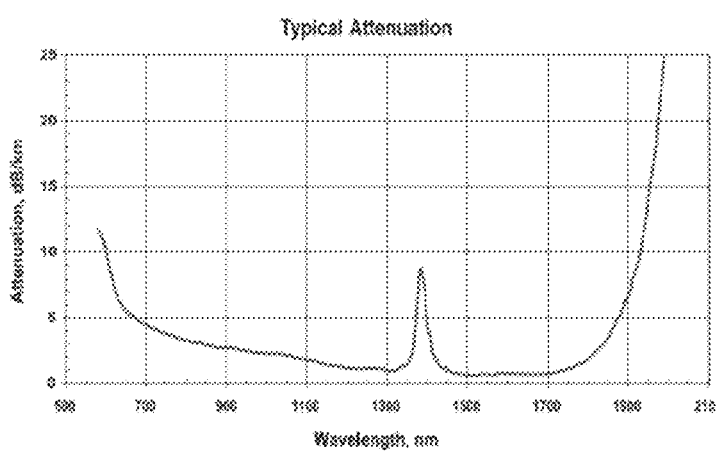
FIG. 2 is a graph illustrating the attenuation of an optical fiber as a function of wavelength, in accordance with the prior art.

When looking at loss curves for multimode fiber products from Fiberguide™, Polymicro™, CeramOptec™ or the like, an example of which is presented in FIG. 2, the minimum loss is less than 1 dB/km and starts to rise significantly at 900 nm, where losses are greater than about 3 dB/km. Each 1 dB/km of additional loss adds a factor of about 10 in loss over about 10 km of total fiber travel or a factor of about 100 for a 10-km link traveled in both directions, for about 20 km of total travel. In addition, what is measured is a change in the optical absorption/loss spectrum shape, where the difference in losses measured at two or more optical wavelengths is the parameter of interest. When the fiber link losses vary by about 3 or about 4 dB/km between two measurement wavelengths (such as between 550 and 600 nm as illustrated in FIG. 2), and for measurements over fiber links of about 10 km for example, small perturbations in the fiber link loss at any of the measurement wavelengths may greatly affect the measurement accuracy. A pulse energy reference is thus needed.

In one embodiment, multimode fibers are used as they can accept much larger pulse energies than single mode fibers, especially in the visible or near infrared where single mode fiber cores are usually less than 5 µm in diameter whereas multimode fibers can have cores of hundreds of microns in diameter. In consequence, multimode fibers allow longer fiber links because the input energies can be higher.

In one embodiment, photon counting detection is used in order to keep the input light energy per pulse as low as possible not to damage the fiber or generate adverse loss generating non-linear effects therein.

While the above description refers to the use of the system 100 in the context of high loss optical links, it should be understood that the system 100 may also be used in a context in which optical links do not present high losses. For example, the pulse generator 102 may be adapted to generate pulses having a wavelength contained in the long haul telecommunications bandwidth such as around 1550 nm.

In the following, exemplary implementations of the optical system 100 are presented.

Figure 3:
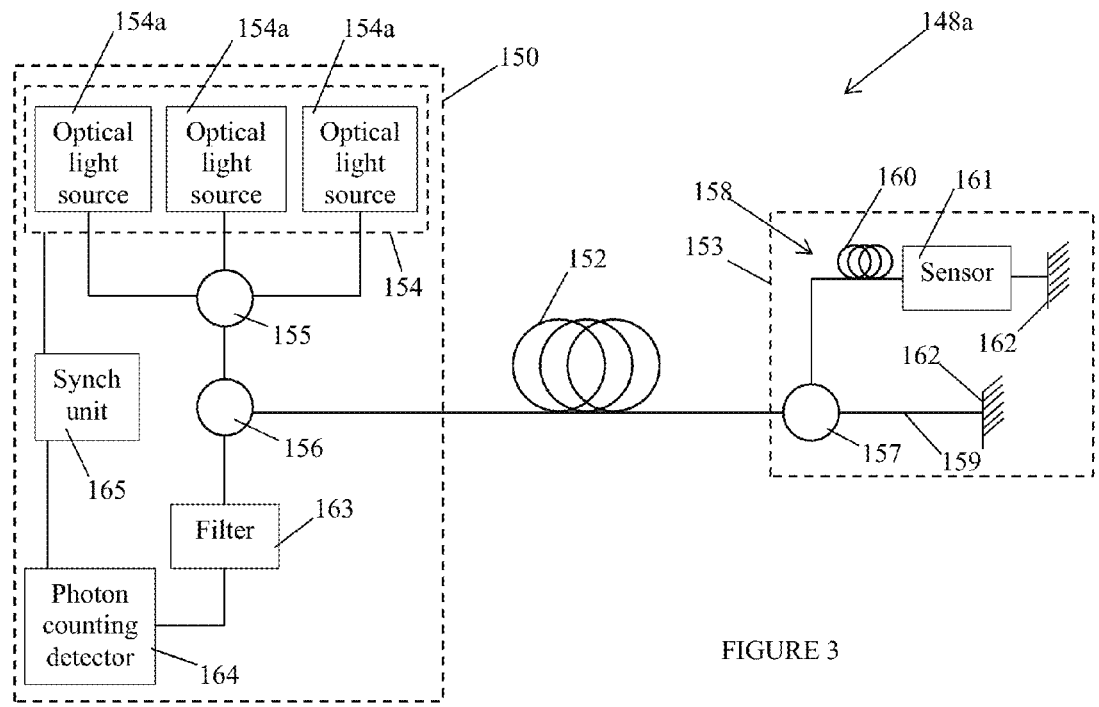
FIG. 3 illustrates an optical measurement system operating in reflection and comprising a single optical link, in accordance with an embodiment.

The optical system 148a illustrated in FIG. 3 comprises an interrogator unit 150, an optical fiber 152, and a sensing unit 153 at the sensor end of the optical fiber 152. The sensing unit 153 comprises a sensing arm 158 which comprises a sensing element or optical loss sensor 161, a delay line 160, and a reflector 162, and a reference arm 159 which comprises an optical waveguide having a predetermined length and a reflector 162. The interrogator unit 150 houses one or multiple optical sources 154 such as lasers. In one embodiment, the interrogator unit 150 comprises three lasers 154a, all having a different emission wavelength, for measuring the difference in optical loss between these wavelengths in the optical loss sensor or sensing element 161 of the sensing unit 153. The lasers may be broad area semiconductor lasers for which the injection current is pulsed and emitting optical pulses of suitable energy. The pulse generator could also be a single laser emitting multiple wavelengths, such as a multi-wavelength dye laser or multi-wavelength optical parametric oscillator. The pulse generator may also be the second harmonic of a Q-switched Nd:YAG laser or pulsed Yb fiber laser or of any other adequate solid state laser. The pulse generator could also be a broadband emitting coherent source of light, covering about 50 nm full width at half maximum for example or engineered to emit light having an optimized spectral shape. The lasers may be pulsed simultaneously and coupled to a single fiber using dichroic filters (bulk or fibered) or beam splitters (bulk or fiber couplers) 155. The lasers could also be pulsed consecutively, one after the other, and coupled to a single fiber using dichroic filters (bulk or fibered) or beam splitters (bulk or fiber couplers) 155. Their pulses may pass through a switch to go from one wavelength to the other. The pulses emitted from fibered optical sources are routed to a fiber optic coupler or circulator (bulk or fibered) 156 and transmitted to the fiber 152. The optical pulse is modified while traveling along the fiber 152. It loses energy because of loss while traveling along the fiber and its temporal shape changes because of optical dispersion, either chromatic or modal.

In one embodiment, optical fibers in the optical fiber links have a spectral attenuation curve, such as that shown in FIG. 2. FIG. 2 shows the attenuation curve for the Ultra Low-OH fiber from Polymicro™. In one embodiment, the range of operation is close to the minimum in attenuation, essentially between the wavelengths 1000 and 1700 nm. For long fiber links, 20 km for example (10 km for getting to the sensor and 10 km return towards the interrogator), the total loss in the optical link using the minimum attenuation of 1 dB/km is 20 dB or a signal 100 times less intense after 20 km of travel than the signal inputted at beginning of the optical fiber link. In the visible wavelengths range, essentially between about 390 and about 700 nm, losses are much higher. With a loss of 11 dB/km at about 600 nm, the total loss would be 220 dB for the same 20 km of fiber travel. That is $10^{22}$ less optical intensity at the output than at the input. Not only the total loss is very important, but the differential loss between any two wavelengths could also be very important. A 1 dB/km difference between two wavelengths adds up to one wavelength having 100 times more loss than the other at the end of the fiber travel. As can be seen from the attenuation curve, this could easily happen in the visible range.

Figure 6:
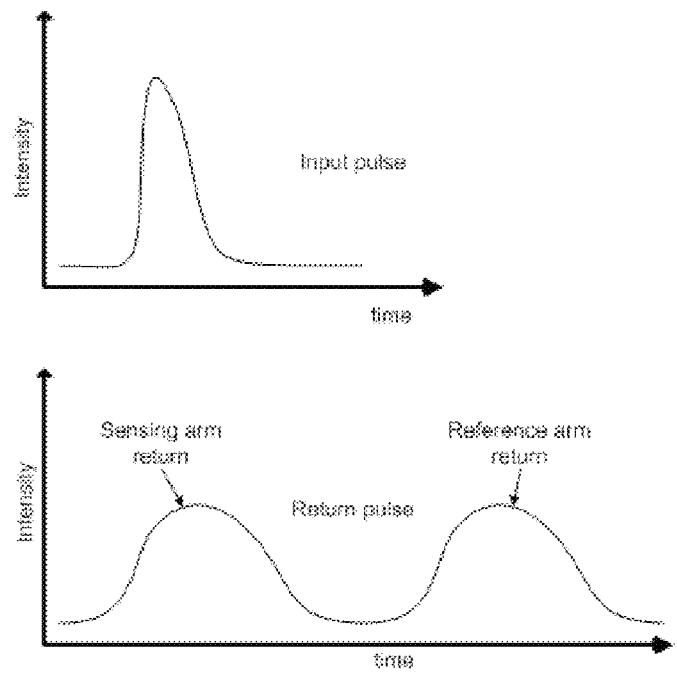
FIG. 6 illustrates the temporal profiles of an input pulse, a sensing pulse, and of a reference pulse, in accordance with an embodiment.

The optical pulse is split into a sensing arm 158 and a reference arm 159 when going through a fiber optic coupler or bulk beam splitter 157. The sensing arm 158 is comprised of an optical delay line 160, made of a piece fiber having a predetermined length for example, a spectro-ratiometric sensor 161 and a reflector 162. The sensing arm 158 is longer than the reference arm 159 in order for the return to be comprised of two distinct optical pulses as illustrated in FIG. 6. The difference in fiber length is predetermined so that the sensing and reference pulses do not overlap in time when reaching the detector 164. The opposite is also possible, namely a sensing arm 158 shorter than the reference arm 159. There is loss in the sensing arm that does not occur in the reference arm 159, owing to the specific function of the optical spectro-ratiometric sensor 161. The reference arm 159 is needed because of probable time varying losses along the fiber that need to be eliminated from the measurement.

In an embodiment in which it is adapted to measure an ion concentration, the spectro-ratiometric sensor 161 can be an optical fiber core surrounded by a special membrane that may contain chromoionophores. When the membrane is in contact with a fluid containing the ions to be detected (such as $Na^+$, $Ca^{2+}$, $K^+$, $Cl^-$, or the like), the shape of the absorption spectrum of the membrane changes, depending on the ion concentration. The light enters the fiber core of the sensor 161 and interacts with the membrane through evanescent waves. The shape of the optical transmission spectrum in the spectro-ratiometric sensor 161 changes with ion concentration and this change in transmission, caused by the change in the shape of the absorption spectrum of the membrane, is measured by the interrogator unit 150. This type of sensor can also be engineered to detect neutral species, in fluids or in gaseous form. It can also be engineered to detect other physical parameters, such as pH. In one embodiment, the spectro-ratiometric sensor 161 comprises a pair of optical collimators mounted face to face in an appropriate mechanical housing, and a filtered gas or fluid flows freely between the collimator pairs. In another embodiment, the spectro-ratiometric sensor 161 comprises an optical collimator-reflector pair for the same use. It should be understood by those skilled in the art that the spectro-ratiometric sensor 161 may take on a large variety of configurations.

Reflecting surfaces 162 are positioned at the end of each arm 158, 159, and the optical sensing and reference pulses are returned and coupled back to the fiber 152 through coupler 157. The pulsing of the optical sources 154*a* is for discriminating between the return from the sensing arm 158 and the return from the reference arm 159, and also to discriminate against other scattering processes such as Rayleigh or Raman backscattering. The return pulses travel along the fiber to the coupler/circulator 156 and are directed to an optical filtering unit 163 that separates the returns from the different lasers 154*a*, when they are simultaneous, and filters them from other in-fiber parasitic processes generated at other wavelengths, then to the detector and ancillary counting electronics 164.

In one embodiment and in order to have the desired signal in a reasonable time, such as in order to have a given signal to noise ratio within a given measurement time, per measurement wavelength, a relatively high energy pulse is outputted from the generator and inputted to the optical fiber link for the most absorbed optical signal. The input light energy per pulse is kept as low as possible not to damage the fiber or induce adverse non-linear effects therein. These thresholds for damage and non-linear effects, along with optical noise sources such as thermal photons, determine the maximum loss or fiber link length that the measurement can support in order to have a specified signal to noise ratio within an imposed measurement time. This input light energy for this maximum length is such that only a few photons per pulse fall onto the detector. It may also occur that less than one photon per pulse falls onto the detector. In these cases, photon counting is used in order to detect an optical signal. This is possible when there are no other sources of optical energy at the wavelengths of measurement other than a few thermal photons. In one embodiment, the photon counting detector is a photomultiplier tube. The photon counting detector may also be a silicon avalanche photodiode in Geiger mode or a so-called solid state photomultiplier, which is an array of silicon avalanche photodiodes in Geiger mode. In another embodiment, the photon counting detector may be a gated photon counting detector in which only the photons received during a temporal counting gate or time window corresponding to one or the other of the return pulses are counted. The use of two counting gates may be preferable, one for the sensing pulse and one for the reference pulse. It may also be possible to do time correlated photon counting inside a single wide temporal gate that encompasses both returns. It will be clear for those skilled in the art that there could be an analog detection part to supplement the photon counting part in order to optimize the dynamic range of the detection. The timing of the counting gates with respect to the input laser pulses is controlled by the synchronization and gating electronics 165.

Figure 4:
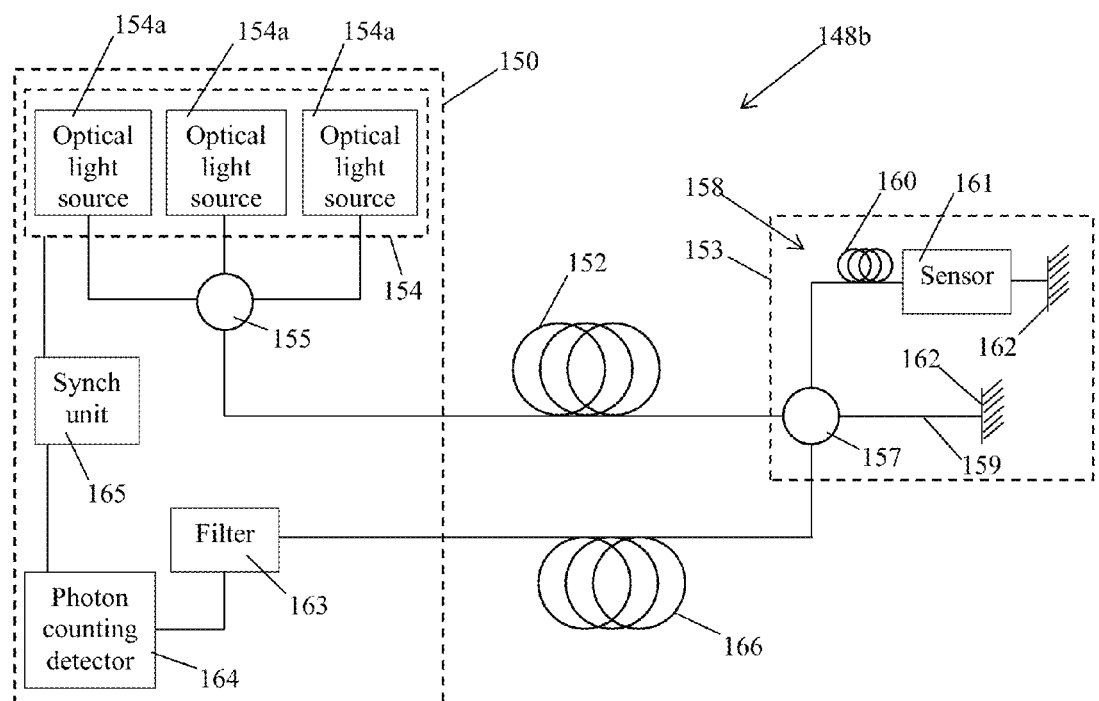
FIG. 4 illustrates an optical measurement system operating in reflection and comprising two single optical links, in accordance with an embodiment.
Figure 5:
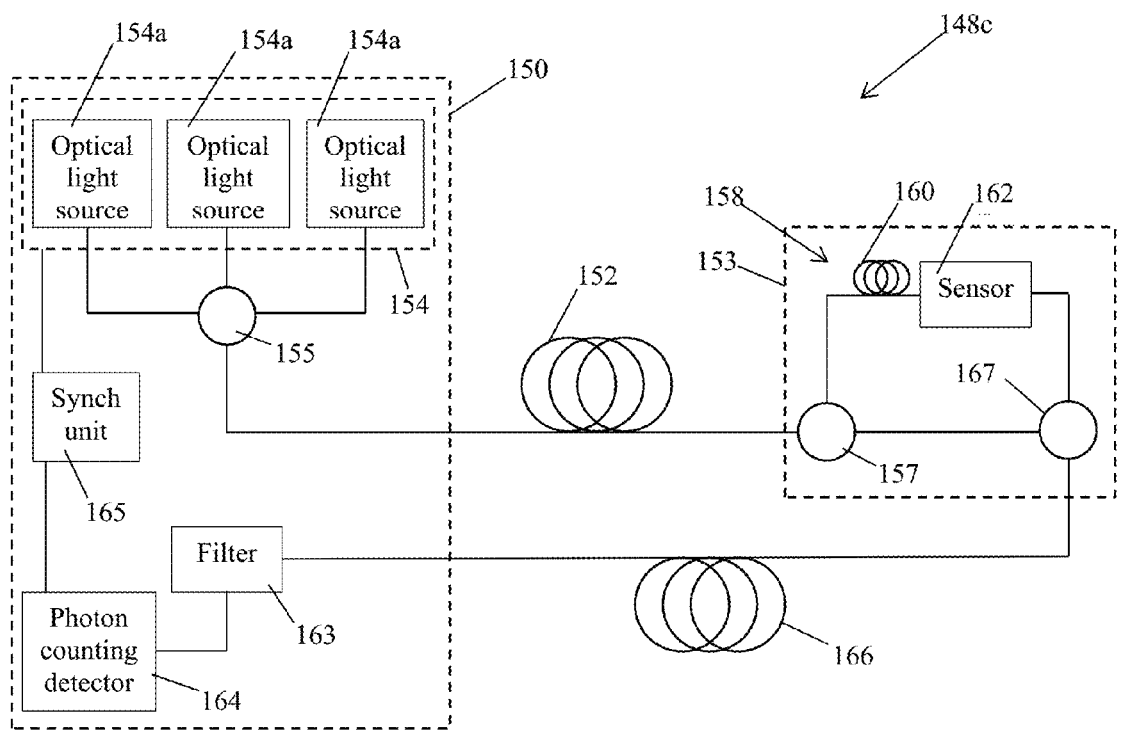
FIG. 5 illustrates an optical measurement system operating in transmission and comprising two optical links, in accordance with an embodiment.

The return fiber can be a different fiber 166 as illustrated in FIG. 4 which illustrates an optical measurement system 148*b* operating in reflection, or the same fiber 152 as illustrated in FIG. 3. The reflecting surfaces 162 could be replaced by an output coupler 167 connected to the return fiber 166 as illustrated in FIG. 5 which illustrates an optical measurement system 148c operating in transmission. When using distinct fibers for channeling the incoming and outgoing pulses, Rayleigh and other backscattering are no longer a concern.

In reflection mode with a single fiber 152, the pulse repetition rate is limited by the round-trip time in the fiber. This is because of parasitic effects such as Rayleigh backscattering. The Rayleigh backscattering of one pulse must not overlap, at least significantly, with the sensor return of another pulse. In embodiments in which a second fiber is used for propagating the sensing and reference pulses, this is not the case, and the pulse repetition rate can be higher and is limited only by the pulse stretching caused by the dispersion effects. This allows for lower input pulse energies.

In one embodiment, the length of the fiber delay 160 essentially depends on modal dispersion when the optical fibers 152, 166 are multimode, and thus on fiber numerical aperture. The lower numerical apertures reduce modal dispersion and delay length, but using such fibers may not always be possible and depends on coupling losses to the spectro-ratiometric sensor 161.

Figure 7:
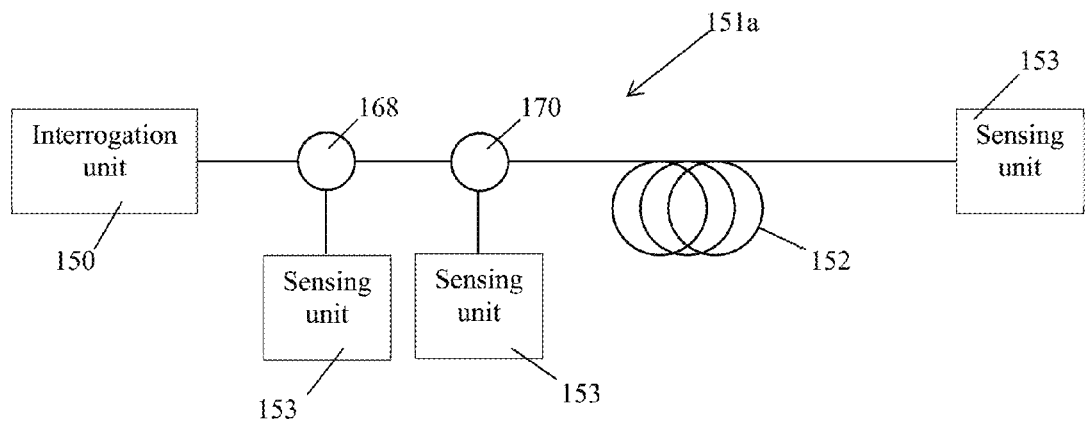
FIG. 7 illustrates an optical measurement system comprising three optical loss sensors connected along a single optical link, in accordance with an embodiment.

In one embodiment, the optical system comprises more than one sensing unit 153. Operating multiple loss sensors on a single fiber optic link may be a requirement in some particular applications. This multiplexing of sensing units could be done in multiple ways such as wavelength division multiplexing or time domain multiplexing. In some cases, the optical signals pass through the sensing unit and continue to travel towards the next sensing unit whereas in other cases light is coupled out of the main fiber line, such as in the optical measurement system 151a illustrated in FIG. 7. The most straightforward coupling scheme is usually to have couplers 168 and 170 presenting the same coupling ratio on all sensing units, for example a 50/50 ratio (or 3 dB coupler). But in the case of a high loss fiber link this would require having a huge dynamic range at the detector end. When the first sensing unit is close to the interrogator unit and is generating much more signal than a sensing unit at the end of the fiber link and at the end of much more fiber loss, the number of sensing units that could be multiplexed on the fiber link for a given minimum signal to noise ratio and measurement time would reduce. For these reasons, the preferred embodiment for multiplexing would be to have a coupling ratio dependent on the distance to the interrogator unit and on the number of multiplexed sensing unit as illustrated in FIG. 7. The closer sensing unit 153 may have a very low coupling to the main fiber link, such as a ratio of 1 part out of a thousand to the sensing unit (1:999), whereas the last sensing unit would be directly on the fiber line 152. The second sensing unit 21 may have a coupling ratio of 1:99 for example. The sensing units 153 may be of the same type. The number of sensing units 153 comprised in the optical system may vary. For example, the optical system may comprise tens of sensing units 153. The coupling ratios are optimized for maximum signal to noise ratios and minimum dynamic range.

Figure 8:
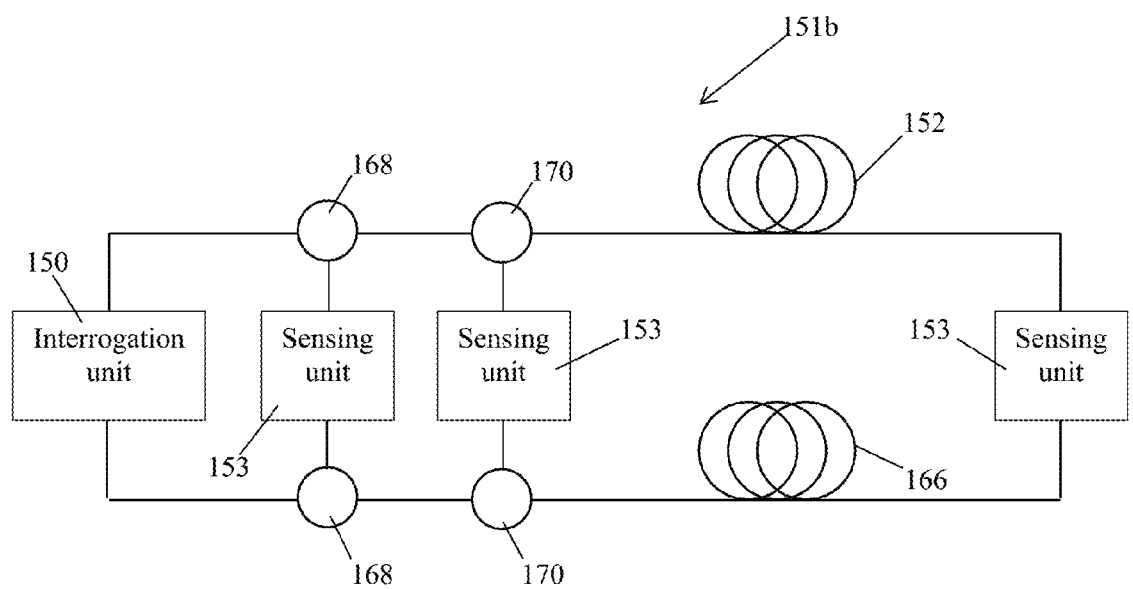
FIG. 8 illustrates an optical measurement system comprising three optical loss sensors connected along two optical links, in accordance with an embodiment.

In the single fiber link scheme illustrated in FIG. 7 above, light traveling towards the next sensing units 153 interferes with the return from the previous sensing unit 153. The Rayleigh backscattering of the pulse traveling towards a given sensing unit 153 will interfere with the measurement of the previous sensing unit 153 in this approach. In one embodiment, the signal traveling towards a given sensing unit 153 is very strong compared to the signal coupled to the previous sensing unit 153 and returned towards the interrogation unit 150. So even though Rayleigh backscattering is weak, it could interfere with the reading of the previous sensing unit 153 when the coupling ratio to sensing unit 153 is very small. It would thus be preferable to have an incoming fiber and an outgoing fiber, thus a two fiber optical measurement system 151b as illustrated in FIG. 8. Couplers 168 and 170 couple out of the fiber and into the fiber respectively with the same ratios. The same applies for the couplers to the other sensing units 153 along the fiber link.

Optical systems comprising an emission sensor for remotely measuring an environmental parameter are described below.

Figure 9:
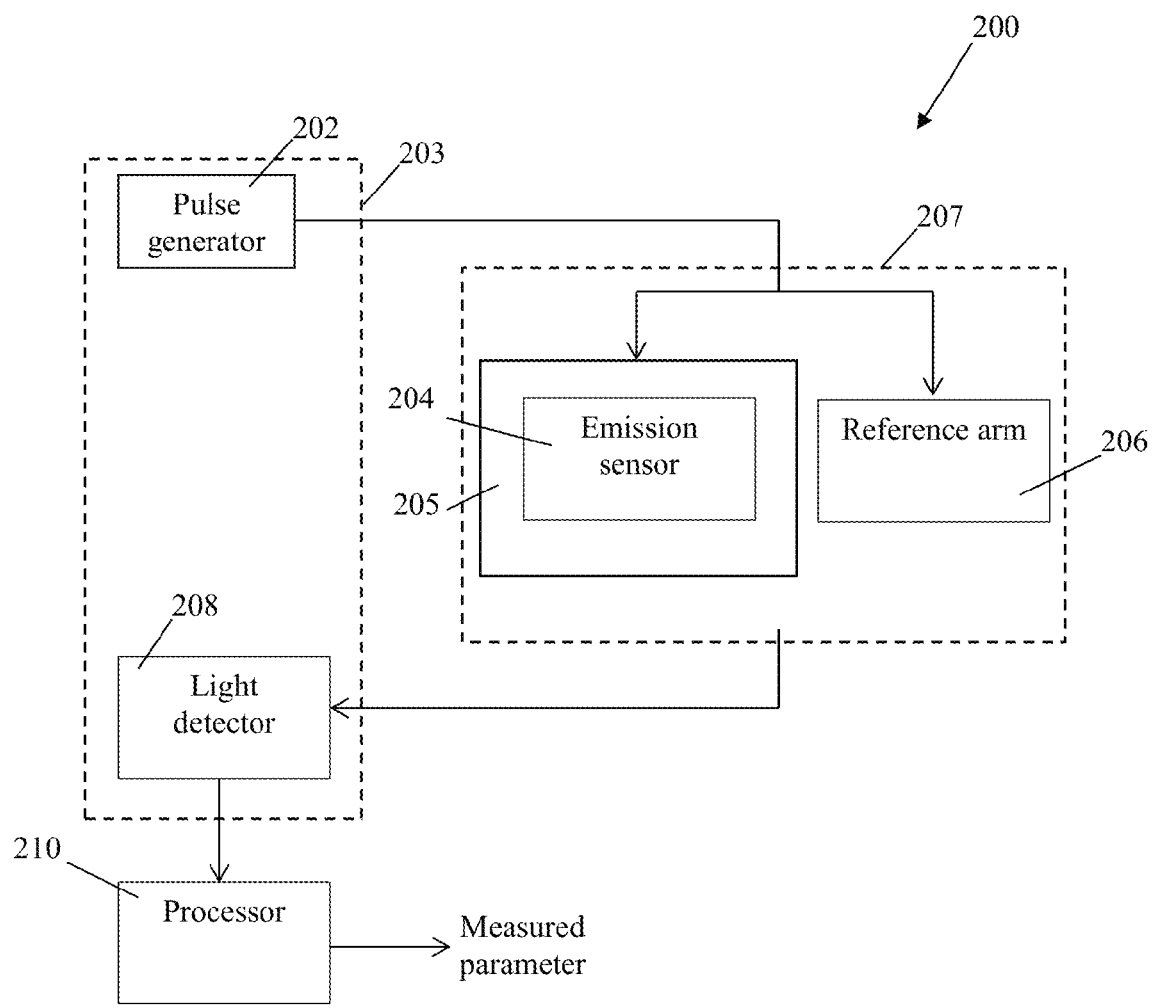
FIG. 9 is a block diagram of an optical measurement system comprising an emission sensor, in accordance with an embodiment.

FIG. 9 illustrates one embodiment of an optical system 200 for remotely measuring an environmental parameter. The environmental parameter may be a physical characteristic of a gas, a solid, or a liquid, an electrical field, or the like. The optical system 200 comprises an optical pulse generator 202, an emission sensor 204, a sensing arm 205 comprising the emission sensor 204, a reference arm 206, a light detector 208, and a processor 210. The pulse generator 202 and the light detector 208 form together an interrogator unit 203. The sensing arm 205 comprising the emission sensor 204 and the reference arm 206 form together a sensing unit 207.

The optical length of the sensing arm 205 is different from that of the reference arm 206 to vary the relative propagation time of the pulses propagating in the arms 205 and 206. For example, a time delay line (not shown) may be inserted in the sensing arm 205 or the reference arm 206.

The pulse generator 202 is adapted to emit optical pulses at at least one wavelength which correspond to the excitation wavelength for the emission sensor. In one embodiment and as described below, the pulse generator 202 may emit first pulses having the excitation wavelength and second pulses having at least one wavelength that is different from the excitation wavelength.

The wavelengths of the pulses emitted by the pulse generator 202 may be in the infrared range such as in the telecommunication bandwidth, the ultraviolet (UV) range, the visible (VIS) range or the near-infrared (NIR) range.

In an embodiment in which it is adapted to emit pulses having different wavelengths, the pulse generator 202 may be adapted to emit the pulses having different wavelengths substantially concurrently. Alternatively, the pulse generator 102 may be adapted to successively emit the pulses having different wavelengths. If the pulses are emitted successively, they must be emitted so that the reference pulses do not arrive concurrently to the measurement pulses created by the excitation pulses.

In one embodiment, the pulse generator 202 comprises a single pulsed light source for emitting the pulses having the excitation wavelength. In another embodiment, the pulse generator 202 comprises a first pulsed light source for emitting pulses having the excitation wavelength and at least one second pulsed light source for emitting pulses having a wavelength that is different from the excitation wavelength. A pulsed light source may be a Q-switched laser, a light source provided with an optical modulator such as an electro-optic modulator, a laser diode of which the current provided by a power supply is modulated for generating pulses, or the like.

An emission sensor is an optical device adapted to receive and absorb light having an excitation wavelength and re-emit light at wavelengths other than the excitation wavelength, and the wavelengths of the light re-emitted by the emission sensor are dependent on an environmental parameter, i.e. a parameter or characteristic of a sample to be sensed. The environmental parameter may be the presence of a gaseous pollutant in the atmosphere surrounding the emission sensor, the presence of impurities in a process, the relative or absolute amount of an ingredient in a mixture or product, a temperature, a pH, an electric field, a magnetic field, or the like. An emission sensor may be used for sensing a parameter of a gas, a liquid, or a solid. It should be understood that an emission sensor may be a spectro-ratiometric sensor.

The light source for exciting the emission sensor may emit light in the UV range, the visible range, the infrared range, or the like, and may be a laser, an LED, a filtered lamp, or the like. The spectral distribution of the excitation light source is chosen such that it does not interfere with the emissions measurement. In one embodiment, the spectral distribution of the excitation light source is less than 10 nm. In the case of Raman excitation, the excitation light source may be chosen to be monochromatic.

For example, in the case of a gas of which a parameter is to be sensed, the excitation light can be tuned to an absorption band of a molecule of interest. Some of the molecules of interest absorb the excitation light (the amount of absorption is dependent on an absorption cross section) and re-emit light in the form of fluorescence at wavelengths higher than that of the excitation light. The amount of light emitted by the emission sensor is also dependent on a parameter called fluorescence quantum efficiency. The wavelengths at which the molecule of interest emits light are often unique to this molecule of interest. By detecting the light emitted by the molecule of interest, it is possible to determine at least the presence of the molecule of interest. Knowing the intensity of the excitation light in the gas, the absorption cross section and the emission quantum efficiency, the optical collection efficiency of the sensing system, the transmission losses through an optical link and through the filtering unit and the detection quantum efficiency, it is possible to also quantify the molecule of interest. The light emitted by the emission sensor may be filtered before being detected. For example, an optical interference filter, a grating spectrometer, an interferometer, or the like may be used.

Another example of an emission sensor is an underwater Raman sensor. Such a sensor can be used to monitor very deep water. A Raman spectrum contains rotational and vibrational signatures of molecules that interact with the excitation light. The excitation light such as monochromatic laser light is directed to an optical fiber. This excitation light can be at 1064 nm in some cases. At the end of the optical fiber, with the emission sensor, the excitation light interacts with the water and generates Raman scattering light. The Raman scattering light is captured and sent back to the surface through an optical fiber. The amplitude of the Raman scattering light at a specific wavelength other than the excitation wavelength or at a plurality of wavelengths other than the excitation wavelength is detected in order to obtain a Raman spectrum. The amplitude at the specific wavelength or the relative amplitudes of at least two components in the Raman spectrum are indicative of the composition of the water at the position of the emission sensor. In order to have a calibrated amplitude measurement, a relative amplitude of the excitation light must be known at the position of the sensor. This can be accomplished by using a stable emission artefact at the position of the sensor. This relative amplitude includes losses in the optical link for both the excitation light and the light emitted at the wavelengths of interest.

In one embodiment and as described below, the pulse generator 202 is adapted to emit pulses having an excitation wavelength and the reference arm 206 comprises an emission artefact adapted to absorb light having the excitation wavelength and emit light having a wavelength different from the excitation wavelength. Each pulse emitted by the pulse generator 202 is split into a sensing pulse which propagates in the sensing arm 205 and a reference pulse which propagates in the reference arm 206. The sensing pulse propagates through the emission sensor 204 which emits a measurement pulse. The reference pulse propagates through the emission artefact which emits a comparison pulse. Both the measurement pulse and the comparison pulse have a same measurement wavelength that is different from the excitation wavelength. A time delay line (not shown) is inserted in one of the sensing and reference arms 204 and 206 in order to delay the propagation of the measurement pulse relative to that of the comparison pulse, or vice versa. The measurement and comparison pulses propagate up to the light detector 208 which detects the pulses and measure their optical energy. The measured optical energy for the measurement and comparison pulses is transmitted to the processor 210 which determines the environmental parameter.

In one embodiment, the light detector 208 detects light at a single wavelength k, i.e. the measurement wavelength. In this case, the parameter may be determined by the processor 210 by calculating the ratio between the measured intensity of the pulse coming from the sensing arm 205 and the measured intensity of the pulse coming from the reference arm 206, which is equal to $(I_s*\epsilon_s(\lambda))/(I_r*\epsilon_r(k))$, where $I_s$ is the intensity of the excitation pulse at the emission sensor 204, $\epsilon_s(\lambda)$ is the emission factor of the emission sensor 204 at the measurement wavelength $\lambda$, $I_r$ is the intensity of the excitation pulse at the emission artefact, $\epsilon_r(\lambda)$ is the emission factor of the emission artefact at the measurement wavelength $\lambda$. The intensity ratio between the intensities $I_s$ and $I_r$ corresponds to the splitting ratio at the measurement wavelength $\lambda$ for the pulses generated by the pulse generator 202 between the sensing and reference arms 205 and 206. By knowing the intensity ratio $(I_s/I_r)$ and calibrating the ratio between the emission factors $\epsilon_s(\lambda)/\epsilon_r(\lambda)$, it is possible to determine the value of $\epsilon_s(\lambda)$ and therefore determine the value of the environmental parameter.

In another embodiment, the light detector is adapted to detect pulses having two different wavelengths, i.e. two different measurement wavelengths $\lambda_1$ and $\lambda_2$. In this case, pulses having the first or second measurement wavelength $\lambda_1$, $\lambda_2$ coming from the sensing arm 205 and pulses having the first or second measurement wavelength $\lambda_1$, $\lambda_2$ coming from the reference arm 206 are detected by the light detector 210. The intensity ratio between the intensity at $\lambda_1$ and the intensity at $\lambda_2$ for the pulses coming from the sensing arm 205, i.e. $I_s(\lambda_1)/I_s(\lambda_2)$, is equal to $\beta_s*(\epsilon_s(\lambda_1)/(\epsilon_s(\lambda_2))*(L(\lambda_1)/(L(\lambda_2))$, where $\epsilon(\lambda_1)$ is the emission factor for the emission sensor 204 at the first measurement wavelength $\lambda_1$, $\epsilon(\lambda_2)$ is the emission factor for the emission sensor 204 at the second measurement wavelength $\lambda_2$, and $\beta_s$ represents the ratio of the losses/efficiencies in the light detector 210 and the sensing coupling ratios between the sensing and reference arms 205 and 206 at the measurement wavelengths. The same applies to the reference arm 206, so that $I_r(\lambda_1)/(I_r(\lambda_2)$ is equal to $\beta_r*(\epsilon_s(\lambda_1)/(\epsilon_s(\lambda_2))*(L(\lambda_1)/(L(\lambda_2))$. The ratio between the intensity ratio for the sensing arm 205 and the intensity ratio for the reference arm 206 is then equal to $(\epsilon_s(\lambda_1)/(\epsilon_s(\lambda_2))/(\epsilon_r(\lambda_1)/(\epsilon_r(\lambda_2))*(\beta_s/\beta_r)$, where $(\beta_s/\beta_r)$ is a constant which depends on the splitting ratio for the measurement pulses between the sensing and reference arms 205 and 206. By calibrating the reference ratio $\epsilon_r(\lambda_1)/\epsilon_r(\lambda_2)$, the sensing ratio $\epsilon_s(\lambda_1)/\epsilon_s(\lambda_2)$ can be known and the environmental parameter can be determined from this sensing ratio.

In another embodiment and as described below, the pulse generator 202 is adapted to emit pulses at at least two different wavelengths, i.e. the excitation wavelength and at least one measurement wavelength. In this case, the reference arm 206 comprises at least an optical waveguide and includes no emission artefact. The pulse generator 202 generates a first pulse having the excitation wavelength and a second pulse having the measurement wavelength. In one embodiment, a beam splitter separates the first and second pulses so that the first pulses propagate in the sensing arm 205 and the second pulses propagate in the reference arm 206. In another embodiment, a coupler such as a 3 dB coupler separates each one of the first and second pulses into a pulse propagating in the sensing arm 205 and a pulse propagating in the reference arm 206. The pulse having the measurement wavelength and propagating in the reference arm 206 propagates up to the light detector 208. The pulse having the excitation wavelength and propagating in the sensing arm 205 excites the emission sensor 204 which in turn emits at least one pulse having the measurement wavelength. The pulse emitted by the emission sensor 204 propagates up to the light detector 208. A time delay is inserted in the sensing arm 205 or the reference arm 206 in order to delay the propagation of the pulses propagating in the sensing and reference arms 205 and 206 relative to one another. The light detector 208 measures the optical energy of the received pulses having the measurement wavelength and transmits the measured energies to the processor 210 which determines the environmental parameter.

In one embodiment, the pulse generator 202 emits first pulses at the excitation wavelength, second pulses at a first measurement wavelength $\lambda_1$ and third pulses at a second measurement wavelength $\lambda_2$. Upon reception of the first pulses, the emission sensor 204 emits pulses having the first measurement wavelength $\lambda_1$ and pulses having the second measurement wavelength $\lambda_2$. The intensity ratio between the intensity at $\lambda_1$ and the intensity at $\lambda_2$ for the pulses coming from the reference arm 206, i.e. $I_r(\lambda_1)/I_r(\lambda_2)$, is equal to $\beta_r*(I_0(\lambda_1)/I_0(\lambda_2))*(L(\lambda_1)/L(\lambda_2))$, where $I_0(\lambda_1)$ is the intensity of the pulse having the first measurement wavelength $\lambda_1$ and emitted by the pulse generator 202, $I_0(\lambda_2)$ is the intensity of the pulse having the second measurement wavelength $\lambda_2$ and emitted by the pulse generator 202, $L(\lambda_1)$ are the losses encountered by the pulses coming from the reference arm 206 having the first measurement wavelength $\lambda_1$, $L(\lambda_2)$ are the losses encountered by the pulses coming from the reference arm 206 and having the second measurement wavelength $\lambda_2$, and $\beta_r$ represents the ratio of the losses/efficiencies in the light detector 210 and the reference coupling ratio between the sensing and reference arms 205 and 206 at the two measurement wavelengths. The intensity ratio between the intensity at $\lambda_1$ and the intensity at 2 for the pulses coming from the sensing arm 205, i.e. $I_s(\lambda_1)/I_s(\lambda_2)$, is equal to $\beta_s*(\epsilon(\lambda_1)/\epsilon(\lambda_2))*(L(\lambda_1)/L(\lambda_2))$, where $\epsilon(\lambda_1)$ is the emission factor for the emission sensor 204 at the first measurement wavelength $\lambda_1$, $\epsilon(\lambda_2)$ is the emission factor for the emission sensor 204 at the second measurement wavelength $\lambda_2$, and $\beta_s$ represents the ratio of the losses/efficiencies in the light detector 210 and the sensing coupling ratio between the sensing and reference arms 205 and 206 (the sensing coupling ratio being equal to one minus the reference coupling ratio).

The ratio between the intensity ratio for the sensing arm 205 and the intensity ratio for the reference arm 206, i.e. $(I_s(\lambda_1)/I_s(\lambda_2))/(I_r(\lambda_1)/I_r(\lambda_2))$, is then equal to $(\beta_s/\beta_r)*(\epsilon(\lambda_1)/\epsilon(\lambda_2))*(I_0(\lambda_2)/I_0(\lambda_1))$. The ratio $((\beta_s/\beta_r)$ can be known using calibration methods and the ratio $(I_0(\lambda_2)/I_0(\lambda_1))$ can be known by measuring the intensity of the pulses emitted by the pulse generator 202 with a calibrated link to the light detector 210. The ratio $(\epsilon(\lambda_1)/\epsilon(\lambda_2))$ can then be determined and the environmental parameter can be determined from this ratio.

In another embodiment, the pulse generator 202 emits first pulses at the excitation wavelength $\lambda_{exc}$ and second pulses at a single measurement wavelength $\lambda_1$. For computing the losses, $I_0(\lambda_1)$ is measured and calibrated with the detector (knowing the splitting ratio and other losses before the detector). This may be done by splitting part of reference pulses and routing the pulses to the detector before inputting into the optical fiber link. The intensity detected by the light detector 210 for the pulse coming from the reference arm 206 at the excitation wavelength $\lambda_{exc}$, i.e. $I_r(\lambda_{exc})$, is equal to $\delta_r(\lambda_{exc})*I_0(\lambda_{exc})*L(\lambda_{exc})$, where $I_0(\lambda_{exc})$ is the intensity of the light having the excitation wavelength $\lambda_{exc}$ at the output of the pulse generator 202, $L(\lambda_{exc})$ are the losses at the excitation wavelength $\lambda_{exc}$, and $\delta_r(\lambda_{exc})$ represents the losses/efficiencies in the optical filtering and detection apparatus at the excitation wavelength $\lambda_{exc}$, along with splitting losses at the sensor end (between the sensing and reference arms). The intensity detected by the light detector 210 for the pulse coming from the reference arm 206 at the measurement wavelength $\lambda_1$, i.e. $I_r(\lambda_1)$, is equal to $\delta_r(\lambda_1)*I_0(\lambda_1)*L(\lambda_1)$, where $I_0(\lambda_1)$ is the intensity of the light having the measurement wavelength $\lambda_1$ at the output of the pulse generator 202, $L(\lambda_1)$ are the losses along the optical path at the measurement wavelength $\lambda_1$, and $\delta_r(\lambda_1)$ represents the losses/efficiencies in the optical filtering and detection apparatus at the measurement wavelength $\lambda_1$, along with splitting losses at the sensor end (between the sensing and reference arms).

The intensity detected by the light detector 210 for the pulse coming from the sensing arm 205 at the measurement wavelength $\lambda_1$, i.e. $I_s(\lambda_1)$, is equal to $\delta_s(\lambda_1)*I_0(\lambda_{exc})*\epsilon(\lambda_1)*(L(\lambda_1)/2)*(L(\lambda_{exc})/2)$, where $I_0(\lambda_{exc})$ is the intensity of the light having the excitation wavelength $\lambda_{exc}$ at the output of the pulse generator 202, $\epsilon(\lambda_1)$ is the emission coefficient of the emission sensor at the measurement wavelength $\lambda_1$, and $\delta_s(\lambda_1)$ represents the losses/efficiencies in the optical filtering and detection apparatus at the measurement wavelength $\lambda_1$, along with splitting losses at the sensor end (between the sensing and reference arms). The ratio of the intensity of the signal from the sensing arm 205 over the product of the intensities of the signals from the reference arm 206 is equal to $\delta_s(\lambda_1)*\epsilon(\lambda_1)/(4*\delta_r(\lambda_1)*\delta_r(\lambda_{exc})*I_0(\lambda_1))$, and allows the determination of $\epsilon(\lambda_1)$ knowing $I_0(\lambda_1)$, $\delta_s(\lambda_1)$, $\delta_r(\lambda_{exc})$ and $\delta_r(\lambda_1)$.

In one embodiment, the reference arm 206 comprises an optical waveguide having a predetermined length. The predetermined length of the reference arm 206 is chosen so as to be different from the length of the sensing arm 205 in order to introduce a time delay between the sensing and reference arms 205 and 206.

In one embodiment, an optical delay line is inserted either in the sensing arm 205 or in the reference arm 206 to induce a time delay between the pulses coming from the arms 205 and 206.

The sensing arm 205 and the reference arm 206 are optically connected to the light detector 210 via an optical waveguide so that the pulses coming from the arms 205 and 206 may propagate up to the light detector 210. It should be understood that any adequate optical link adapted to propagate optical pulses may be used. In one embodiment, the optical link is an optical fiber. The optical fiber may be single mode at the wavelengths of the light pulses. Alternatively, the optical fiber may be multimode at the wavelengths of the light pulses.

In one embodiment, the sensing arm 205 and the reference arm 206 are connected to the light detector 210 via the same optical waveguide that connects the pulse generator 202 to the sensing and reference arms 205 and 206.

In an embodiment in which the reference arm 206 comprises an emission artefact, the sensing and reference arms 205 and 206 may be connected to the light detector 210 via an optical waveguide that is different from the optical waveguide that connects the pulse generator 202 to the sensing and reference arms 205 and 206.

In the following, exemplary embodiments of the system 200 are described.

Figure 10:
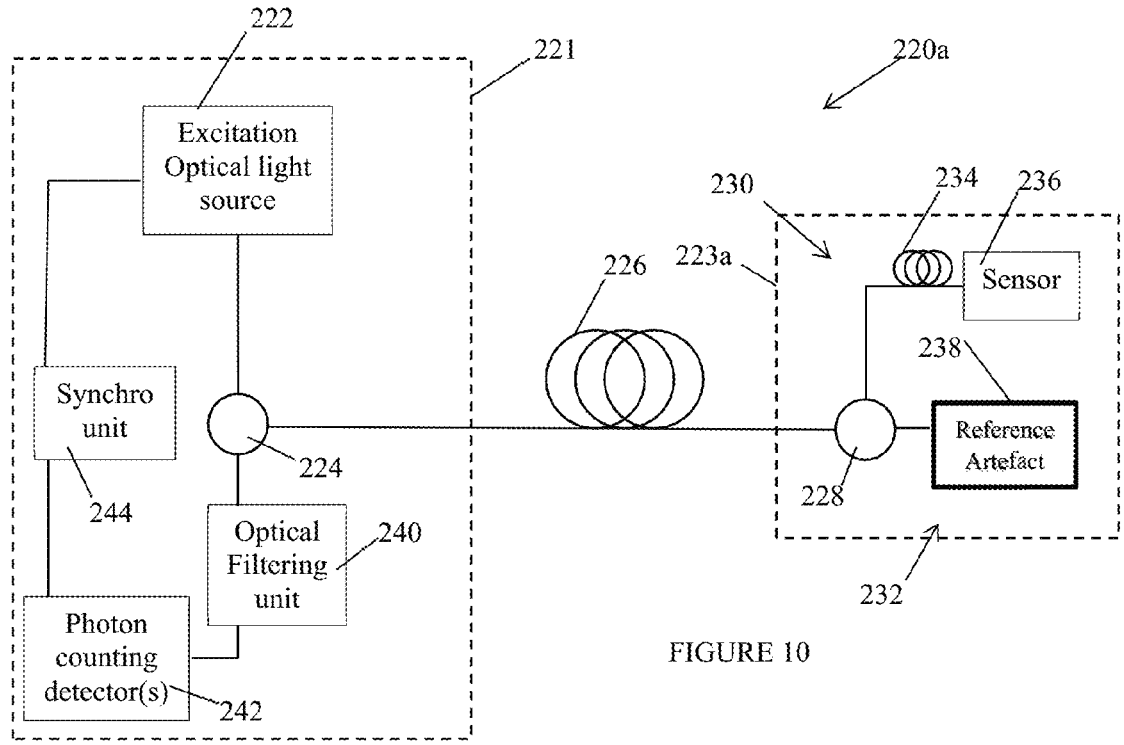
FIG. 10 illustrates an optical measurement system operating in reflection and comprising an emission artefact and a single optical link, in accordance with an embodiment.
Figure 11:
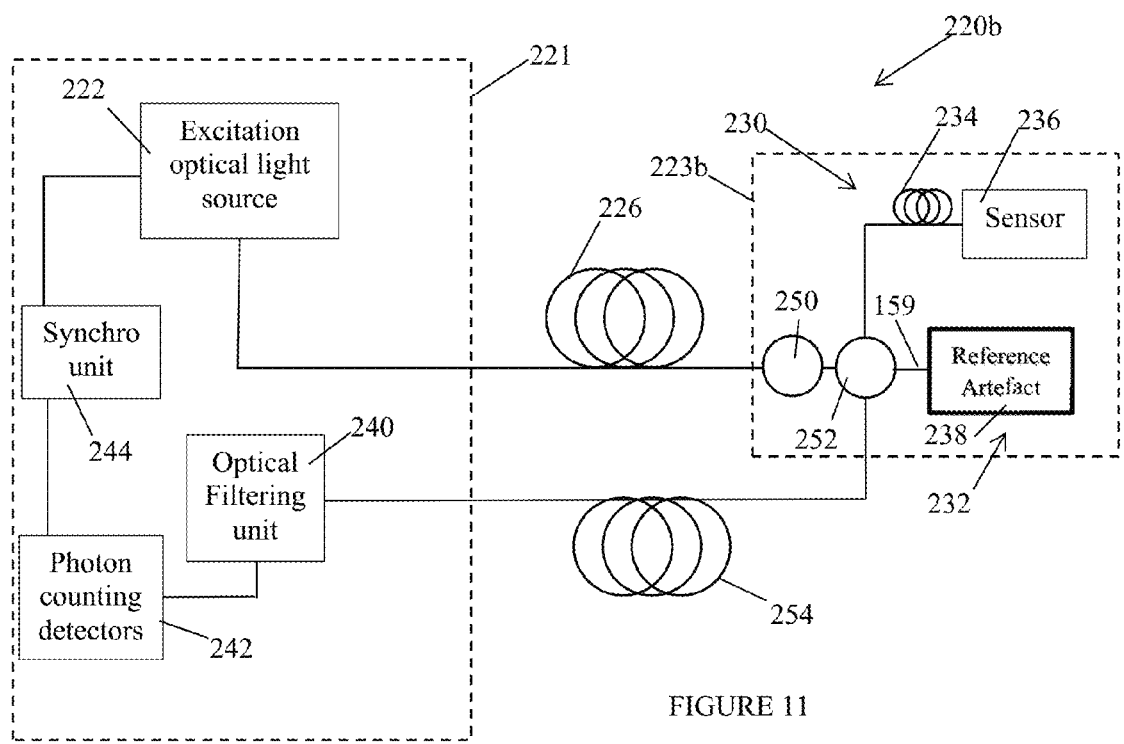
FIG. 11 illustrates an optical measurement system operating in reflection and comprising an emission artefact and two optical links, in accordance with an embodiment.
Figure 12:
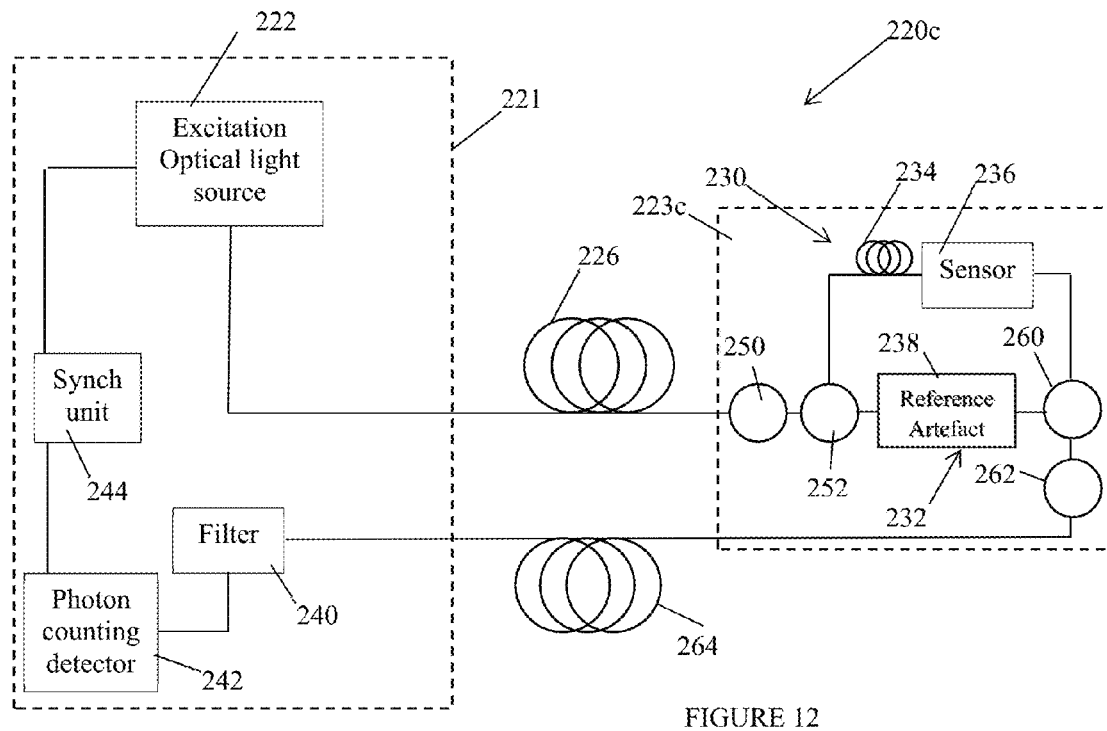
FIG. 12 illustrates an optical measurement system operating in transmission and comprising an emission artefact and two optical links, in accordance with an embodiment.

FIGS. 10-12 each illustrate a respective exemplary embodiment of the system 200 in which an emission artefact is included in the reference arm.

Referring to FIG. 10, there is illustrated an exemplary optical system 220a for sensing an environmental parameter of a sample being in contact or in proximity with an emission sensor. The system 220a comprises an interrogation unit 221 and a sensing unit 223a which are optically connected together by an optical link.

The system 220a comprises a pulsed light source 222 adapted to emit light pulses at an excitation wavelength. The pulsed light source 222 is optically connected to a circulator 224 which propagates the pulses generated by the pulsed light source 222 in an optical fiber 226. The optical fiber 226 is connected a beam splitter 228 which is optically connected to a sensing arm 230 and a reference arm 232. The beam splitter 228 is adapted to split each pulse coming from the pulsed light source 222 into a sensing pulse that propagates in the sensing arm 230 and a reference pulse that propagates in the reference arm 232. Alternatively, a fiber optic coupler such as a 3 dB coupler may be used for splitting the pulses.

The sensing arm 230 comprises a time delay line 234 and an emission sensor 236 while the reference arm 232 comprises an emission artefact. The sensing pulse coming from the beam splitter 228 propagates into the emission sensor 236. The emission sensor 236 emits light at a wavelength different from that of the sensing pulse, i.e. different from the excitation wavelength. In particular, the emission sensor 236 emits a first measurement pulse having a measurement wavelength which propagates towards the time delay line 234 and the beam splitter 228. It should be understood that the part of the sensing pulse that is not converted into the first measurement pulse does not propagate back towards the beam splitter 228. The reference pulse coming from the beam splitter 228 propagates into the emission artefact 238. The emission artefact 238 emits light at the same wavelength as that of the first measurement pulse of the emission sensor 236. In particular, the emission artefact 238 emits a second measurement pulse having the measurement wavelength which propagates towards the beam splitter 228. It should be understood that the part of the reference pulse that is not converted into the second measurement pulse does not propagate back towards the beam splitter 228.

It should be understood that the time delay line 234 delays the propagation of the first measurement pulse relative to that of the second measurement pulse. It should also be understood that the time delay line could be contained in the reference arm 232.

The beam splitter 228 propagates the first and second measurement pulses in the optical fiber 226. The circulator 224 propagates the first and second measurement pulses towards an optical filtering unit 240 that filters the first and second measurement pulses from other in-fiber parasitic processes generated at other wavelengths. The first and second measurement pulses then propagate up to a photon counting detector 242 which successively detects the second measurement pulse and the first measurement pulse. The photon counting detector 242 further measures the intensity of the first and second measurement pulses.

In one embodiment and as described above, the timing of the emission of the excitation pulses and that of the detection of the first and second measurement pulses are controlled by a synchronization and gating electronics 244.

While in the system 220a a single optical link optically connects the interrogation unit 221 and the sensing unit 223b, FIG. 11 illustrates an exemplary system 220b in which two optical links connect the interrogation unit 221 and the sensing unit 223b. The system 220b comprises the interrogation unit 221 which is identical to that of the system 220a, and a sensing unit 223b. An optical link 226 such as an optical fiber optically connects the pulsed light source 222 of the interrogation unit 221 to the sensing unit 223b. The sensing unit 223b comprises a dichroic beam splitter 250, a beam splitter or coupler 252, a sensing arm 230, and a reference arm 232. The dichroic beam splitter 250 is connected to the optical fiber 226 to receive the excitation pulses generated by the pulsed light source 222. The dichroic beam splitter 250 lets the excitation pulses propagating therethrough and filters the fluorescence or other emissions from the optical link 226 so that it does not interfere with the measurement. A beam splitter or coupler 252 is connected to the dichroic beam splitter 250 and is adapted to split each excitation pulse into a sensing pulse and a reference pulse. The sensing pulse coming from the beam splitter 252 propagates into the time delay line 234 and the emission sensor 236. The emission sensor 236 emits light at a wavelength different from that of the sensing pulse, i.e. different from the excitation wavelength. In particular, the emission sensor 236 emits a first measurement pulse having a measurement wavelength which propagates towards the time delay line 234 and the beam splitter 252. The reference pulse coming from the beam splitter 252 propagates into the emission artefact 238. The emission artefact 238 emits light at the same wavelength as that of the first measurement pulse of the emission sensor 236. In particular, the emission artefact 238 emits a second measurement pulse having the measurement wavelength which propagates towards the beam splitter 252.

The beam splitter 252 propagates the first and second measurement pulses in a second optical link 254 such as a second optical fiber. The second optical fiber 254 is optically connected to the optical filtering unit 240. The first and second measurement pulses are then detected by the photon counting detector 242 after being filtered by the optical filtering unit 240.

While in the exemplary embodiments illustrated in FIGS. 10 and 11, the system 220a and 220b operate in back-scattering, i.e. the first and second emitted pulses propagates back towards the beam splitter 228, 252, FIG. 12 illustrates an exemplary system 220c that operates in transmission. The system 220c comprises an interrogation unit 221 which is identical to that of the systems 220a and 220b, and a sensing unit 223c which is connected to the interrogation unit 221 via an optical link 226.

The sensing unit 223c comprises the dichroic beam splitter 250, the beam splitter 252, the sensing arm 230, and the reference arm 232, which are all contained in the sensing unit of the system 220b, and further comprises a beam combiner 260 and a second dichroic splitter 262. As in the system 220b, the dichroic beam splitter 250 is connected to the optical fiber 226 to receive the excitation pulses generated by the pulsed light source 222. The second dichroic beam splitter 262 is optically connected to the first end of a second optical link 264 of which the second end is connected to the optical filtering unit 240.

The dichroic beam splitter 250 lets the excitation pulses propagating therethrough and filters the fluorescence or other emissions from the optical link 226 so that it does not interfere with the measurement. The beam splitter or coupler 252 is connected to the dichroic beam splitter 250 and is adapted to split each excitation pulse into a sensing pulse and a reference pulse. The sensing pulse coming from the beam splitter 252 propagates into the time delay line 234 and the emission sensor 236. The emission sensor 236 emits light at a wavelength different from that of the sensing pulse, i.e. different from the excitation wavelength. In particular, the emission sensor 236 emits a first measurement pulse having a measurement wavelength which propagates away from the time delay line 234 towards the beam combiner 260. The reference pulse coming from the beam splitter 252 propagates into the emission artefact 238. The emission artefact 238 emits light at the same wavelength as that of the first measurement pulse of the emission sensor 236. In particular, the emission artefact 238 emits a second measurement pulse having the measurement wavelength which propagates away from the beam splitter 252 towards the beam combiner 260.

The beam combiner 260 combines the first and second measurement pulses into an optical link which is connected to the second dichroic beam splitter. The second dichroic beam splitter 262 lets the first and second measurement pulses propagating therethrough and filters the residual excitation pulse so that it does not generate fluorescence or other emissions in the optical link 264 so that it does not interfere with the measurement. The first and second measurement pulses then propagates in the optical fiber 264 up to the optical filtering unit 240 and the photon counting detector 242.

It should be understood that in the systems 220a, 220b, and 220c, a single measurement wavelength may be detected by the photon counting detector 242. Alternatively, two or more different measurement wavelengths may be detected by the photon counting detector 242.

Figure 13:
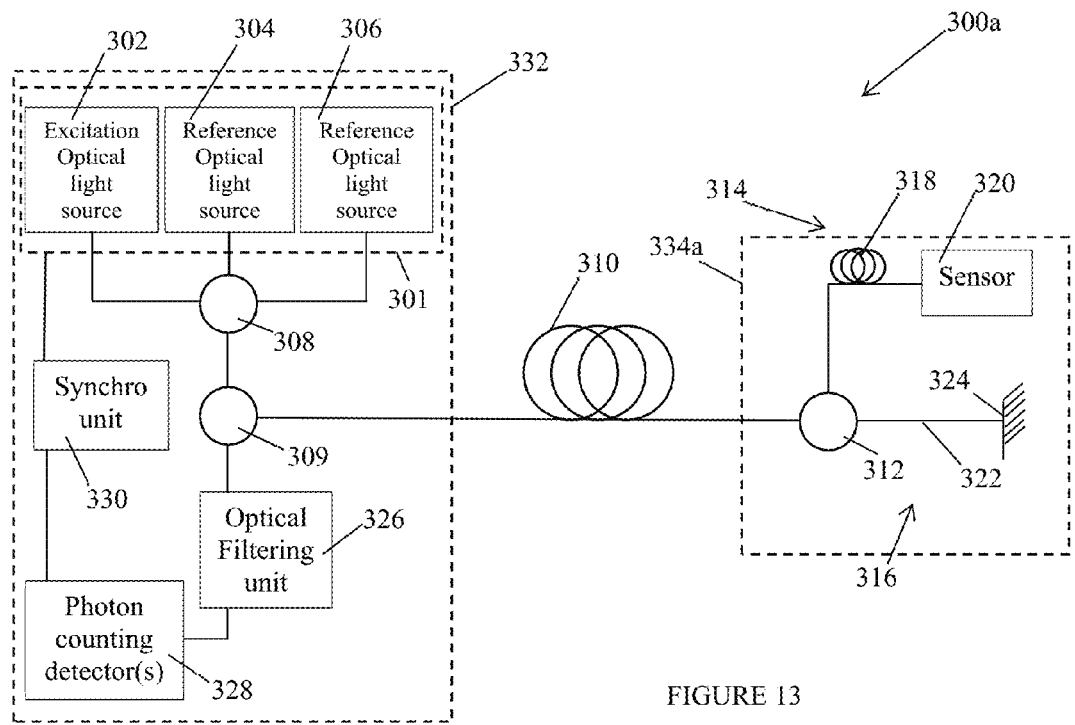
FIG. 13 illustrates an optical measurement system comprising no emission artefact, in accordance with a first embodiment.
Figure 14:
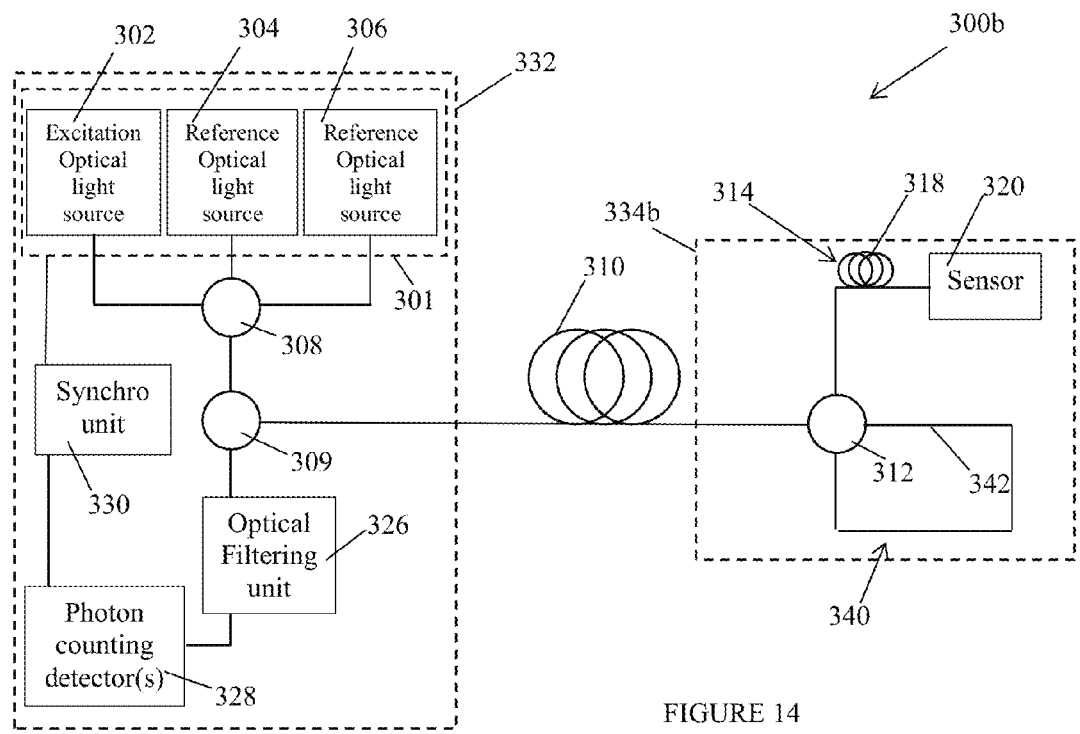
FIG. 14 illustrates an optical measurement system comprising no emission artefact, in accordance with a second embodiment.
Figure 15:
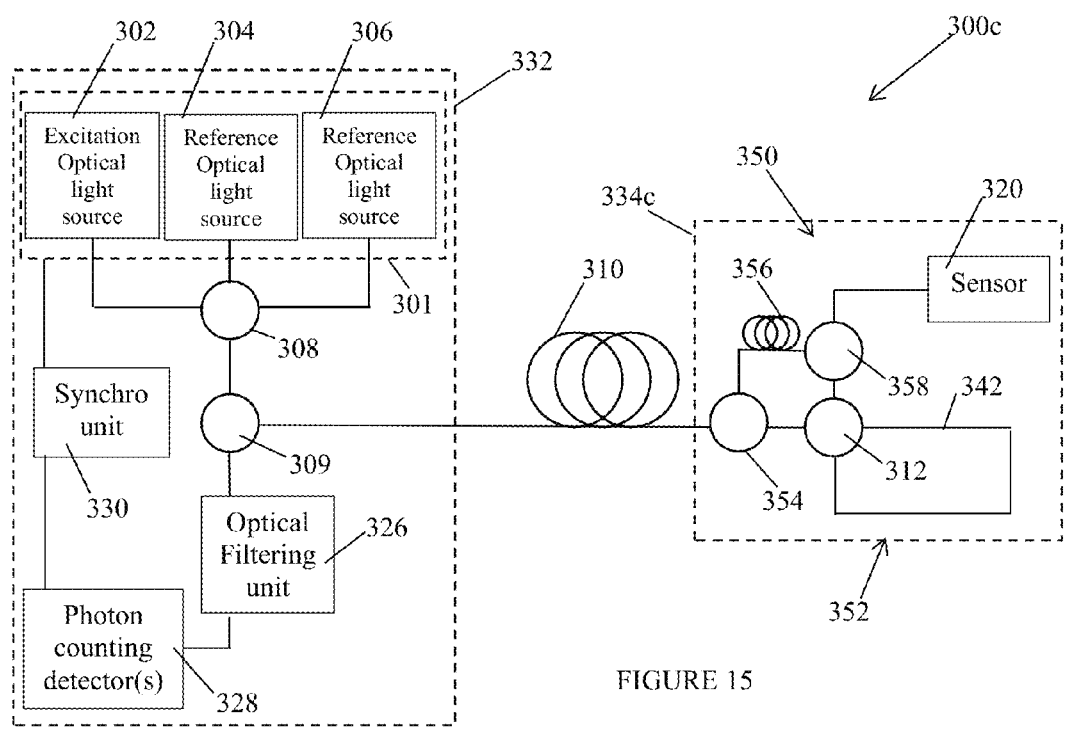
FIG. 15 illustrates an optical measurement system comprising no emission artefact, in accordance with a third embodiment.

FIGS. 13-15 each illustrate a respective exemplary embodiment of the system 200 in which the reference arm comprises no emission artefact.

Referring to FIG. 13, there is illustrated an exemplary optical system 300a for sensing an environmental parameter of a sample being in contact or in proximity with an emission sensor.

The system 300a comprises a light source 301 which includes an excitation pulse source 302 adapted to emit optical pulses having an excitation wavelength, a first reference pulse source 304 adapted to emit first pulses having a first measurement wavelength, and a second reference pulse source 306 adapted to emit second pulses having a second measurement wavelength. A combiner 308 combines together the pulses emitted by the sources 302, 304, and 306, and propagates the pulses towards an optical coupler 309. The coupler 309 is optically connected to an optical link 310 and an optical filtering unit 326. The coupler splits the first pulses into first reference pulses which propagate in the optical link 310 and first sampling pulses which propagate towards the optical filtering unit 326. The coupler also splits the second pulses into second reference pulses which propagate in the optical link 310 and second sampling pulses which propagate towards the optical filtering unit 326.

The first and second reference pulses propagate along the optical link 310 up to a beam splitter 312. The beam splitter 312 is connected to a sensing arm 314 and a reference arm 316. The sensing arm 314 comprises a time delay line 318 and an emission sensor 320 while the reference arm 316 comprises an optical waveguide 322 and an optical reflector 324, such as a mirror, adapted to reflect the first and second measurement wavelengths.

The beam splitter 312 directs the excitation pulses in the sensing arm 314 towards the time delay line 318 and the first and second reference pulses in the reference arm 316 towards the optical reflector 324. Each excitation pulse is received by the emission sensor 320 which in turn emits a first measurement pulse having the measurement wavelength and a second measurement pulse having the second measurement wavelength. The first and second measurement pulses propagate in the time delay line 318 up to the beam splitter 312. The first and second reference pulses propagate along the optical link 322 in the reference arm 316 and are reflected towards the beam splitter 312 by the optical reflector 324. The beam splitter 312 propagates the first and second measurement pulses and the first and second reference pulses in the optical fiber 310. The first and second measurement pulses and the first and second reference pulses propagate along the optical fiber 310 and are directed towards the optical filtering unit 326 by the optical coupler 309 before reaching the photon counting detector 328.

The photon counting detector measures the optical intensity of the first and second sampling pulses, and that of the first and second measurement pulses and the first and second reference pulses. The measured intensities are transmitted to a processor which determines the value of the environmental parameter using at least the measured intensities.

In one embodiment and as described above, the timing of the emission of the pulses by the sources 302, 304, and 306, and that of the detection of the first and second sampling pulses, the first and second measurement pulses, and the first and second reference pulses are controlled by a synchronization and gating electronics 330.

In one embodiment, the beam splitter 312 is an optical coupler. In this case, part of the excitation pulse propagates in the reference arm 316, and the optical reflector is adapted to not reflect the excitation wavelength. Similarly, part of the references pulses propagates in the sensing arm 314. In this case, the sensing arm 314 is adapted not to reflect the portion of the reference pulses propagating therein.

While the system 300a comprises two reference pulse sources 304 and 306 for emitting pulses at two different measurement wavelengths, it should be understood that one of the two reference pulse sources 304 and 306 may be omitted so that only one measurement wavelength be considered and measured by the detector 328.

While the system 300a comprises an optical reflector 324 for reflecting the reference pulses, the system 300b illustrated in FIG. 14 comprises a sensing unit 334b in which only an optical waveguide 342 which forms a loop in a reference arm 340. The optical waveguide has a first end connected to a given port of the beam splitter 312 for receiving the first and second reference pulses therefrom, and a second end connected to another port of the beam splitter 312 for coupling the first and second reference pulses into the optical fiber 310.

Similarly to the system 300a, the system 300b may operate with a single measurement wavelength. In this case, one of the two reference pulse sources 304 and 306 is omitted so that only one measurement wavelength be considered and measured by the detector 328.

FIG. 15 illustrates a further exemplary system 300c for sensing an environmental parameter. The system 300c comprises a sensing unit 334c including a sensing arm 350, a reference arm 352, and a dichroic beam splitter 354 to which the sensing and reference arms 350 and 352 are optically connected. The sensing arm 350 comprises a time delay line 356, a second dichroic beam splitter 358, and an emission sensor 320. The reference arm 352 comprises a beam splitter 312 and a waveguide 342 of which the ends are connected to the beam splitter 312. The beam splitter is further optically connected to the second dichroic beam splitter 358.

In operation, the pulses generated by the sources 302, 304, and 306 are split by the dichroic beam splitter 354. The excitation pulses are propagated in the sensing arm 350 while the first and second reference pulses are propagated in the reference arm 352. The excitation pulse propagates in the time delay line before being directed towards the emission sensor 320 by the second dichroic beam splitter 358. The emission sensor 320 converts the excitation pulse into a first measurement pulse having the first measurement wavelength and a second measurement pulse having the second measurement wavelength. The first and second measurement pulses propagate up to the second dichroic beam splitter 358 which directs them towards the beam splitter 312. The beam splitter 312 then directs the first and second measurement pulses towards the first dichroic beam splitter 354 which couples them into the optical fiber 310.

The first and second reference pulses propagate from the first dichroic beam splitter 354 to the beam splitter 312. The beam splitter 312 couples the first and second reference pulses into the optical waveguide 342 before returning back to the beam splitter 312 which directs them to the first dichroic beam splitter 354. The first dichroic beam splitter 354 couples the first and second reference pulses into the optical fiber 310.

The first and second measurement pulses and the first and second reference pulses are detected by the photon counting detector 328 after propagating through the optical filtering unit. The value of the environmental parameter may then be determined using the measured intensity of the sampling pulses, the first and second measurement pulses, and the first and second reference pulses.

Similarly to the systems 300a and 300b, the system 300c may operate with a single measurement wavelength. In this case, one of the two reference pulse sources 304 and 306 is omitted so that only one measurement wavelength be considered and measured by the detector 328.

It should also be understood that the loop waveguide 342 may be replaced by a reflector such as the optical reflector 324 illustrated in FIG. 13.

The embodiments of the invention described above are intended to be exemplary only. The scope of the invention is therefore intended to be limited solely by the scope of the appended claims.

I claim:

1. An optical system for sensing an environmental parameter of a sample, comprising:
    an optical pulse generator for generating an excitation pulse having an excitation wavelength;
    a pulse splitter for splitting the excitation pulse into a sensing pulse and a reference pulse;
    a sensing arm connected to the pulse splitter for receiving the sensing pulse therefrom, the sensing arm comprising an optical emission sensor for sensing the environmental parameter of the sample, the optical emission sensor generating at least one first measurement pulse, each first measurement pulse having a respective measurement wavelength different from the excitation wavelength;
    a reference arm connected to the pulse splitter for receiving the reference pulse therefrom, the reference arm comprising an emission artefact adapted to convert the reference pulse into at least one second measurement pulse each having the respective measurement wavelength;
    a time delay line contained in one of the sensing arm and the reference arm, the time delay line for delaying a propagation of one of the at least one first measurement pulse and the at least one second measurement pulse relative to a propagation of another one of the at least one first measurement pulse and the at least one second measurement pulse;
    a light detector for detecting the at least one first measurement pulse and the at least one second measurement pulse and measuring an optical energy of the at least one first measurement pulse and the at least one second measurement pulse; and
    at least one optical link for optically connecting the pulse generator to the pulse splitter, and the sensing and reference arms to the light detector.

2. The optical system of claim 1, wherein the at least one optical link comprises a single optical link, the at least one first measurement pulse and the at least one second measurement pulse corresponding to back-scattered light emitted by the emission sensor and the emission artefact, respectively.

3. The optical system of claim 1, wherein the at least one optical link comprises a first optical link for optically connecting the pulse generator to the pulse splitter, and a second optical link for optically connecting the sensing and reference arms to the light detector.

4. The optical system of claim 3, wherein the at least one first measurement pulse and the at least one second measurement pulse correspond to back-scattered light emitted by the emission sensor and the emission artefact, respectively.

5. The optical system of claim 3, wherein the at least one first measurement pulse and the at least one second measurement pulse correspond to forward-scattered light emitted by the emission sensor and the emission artefact, respectively.

6. A method for remotely sensing an environmental parameter, comprising:
    generating an excitation pulse having an excitation wavelength;
    propagating the excitation pulse along at least one optical link;
    splitting the excitation pulse into a sensing pulse and a reference pulse;
    propagating the sensing pulse in a sensing arm, the sensing arm comprising an emission sensor, thereby sensing the environmental parameter and generating at least one first measurement pulse, each first measurement pulse having a respective measurement wavelength different from the excitation wavelength;
    propagating the reference pulse in a reference arm, the sensing arm comprising an emission artefact, thereby generating at least one second measurement pulse, each second measurement pulse having the respective measurement wavelength;
    delaying a propagation of one of the at least one first measurement pulse and the at least one second measurement pulse relative to a propagation of another one of the at least one first measurement pulse and the at least one second measurement pulse;
    propagating the at least one first measurement pulse and the at least one second measurement pulse in the at least one optical link; and
    measuring an optical energy of the at least one first measurement pulse and the at least one second measurement pulse.

7. The method of claim 6, wherein said propagating the excitation pulse along at least one optical link comprises propagating the excitation pulse along a single optical link, and said propagating the at least one first measurement pulse and the at least one second measurement pulse in the at least one optical link comprises propagating the at least one first measurement pulse and the at least one second measurement pulse along the single optical link, the at least one first measurement pulse and the at least one second measurement pulse corresponding to back-scattered light emitted by the emission sensor and the emission artefact, respectively.

8. The method of claim 6, wherein said propagating the excitation pulse along at least one optical link comprises propagating the excitation pulse along a first optical link, and said propagating the at least one first measurement pulse and the at least one second measurement pulse in the at least one optical link comprises propagating the at least one first measurement pulse and the at least one second measurement pulse along the second optical link different from the first optical link.

9. The method of claim 8, wherein the at least one first measurement pulse and the at least one second measurement pulse correspond to back-scattered light emitted by the emission sensor and the emission artefact, respectively.

10. The method of claim 8, wherein the at least one first measurement pulse and the at least one second measurement pulse correspond to forward-scattered light emitted by the emission sensor and the emission artefact, respectively.

11. An optical system for sensing an environmental parameter of a sample, comprising:
    an optical pulse generator for generating an excitation pulse having an excitation wavelength and at least one reference pulse, each one of the at least one reference pulse having a respective measurement wavelength different from the excitation wavelength;
    a sensing arm optically connected to the optical pulse generator for receiving at least a portion of the excitation pulse therefrom, the sensing arm comprising an optical emission sensor for sensing the environmental parameter; the optical emission sensor generating at least one measurement pulse each having the respective measurement wavelength;
    a reference arm optically connected to the optical pulse generator for receiving the at least one reference pulse therefrom;
    a time delay line contained in one of the sensing arm and the reference arm, the time delay line for delaying a propagation of one of the at least one measurement pulse and the at least one reference pulse relative to a propagation of another one of the at least one measurement pulse and the at least one reference pulse;
    a light detector for detecting the at least one measurement pulse and the at least one reference pulse and measuring an optical energy of the at least one measurement pulse and the at least one reference pulse; and
    an optical link for optically connecting the pulse generator to the sensing and reference arms, and the sensing and reference arms to the light detector.

12. The optical system of claim 11, further comprising a beam splitter optically connected to the optical link and the sensing and reference arms for propagating the excitation pulse into the sensing arm and the at least one reference pulse into the reference arm.

13. The optical system of claim 12, wherein the reference arm comprises an optical reflector adapted to reflect the at least one reference pulse.

14. The optical system of claim 12, wherein the reference arm comprises an optical loop.

15. The optical system of claim 11, further comprising an optical coupler optically connected to the optical link and the sensing and reference arms for propagating at least a portion of the excitation pulse into the sensing arm and at least a portion of the at least one reference pulse into the reference arm.

16. A method for remotely sensing an environmental parameter, comprising:
    generating an excitation pulse having an excitation wavelength and at least one reference pulse, each one of the at least one reference pulse having a respective measurement wavelength different from the excitation wavelength;
    propagating the excitation pulse and the at least one reference pulse along an optical link;
    propagating the excitation pulse in a sensing arm, the sensing arm comprising an emission sensor, thereby sensing the environmental parameter and generating at least one measurement pulse each having the respective measurement wavelength;
    propagating the at least one reference pulse in a reference arm;
    delaying a propagation of one of the at least one measurement pulse and the at least one reference pulse relative to a propagation of another one of the at least one measurement pulse and the at least one reference pulse;
    propagating the at least one measurement pulse and the at least one reference pulse in the optical link; and
    measuring an optical energy of the at least one measurement pulse and at least one reference pulse.

17. The method of claim 16, further comprising propagating the excitation pulse and the at least one reference pulse into a beam splitter optically connected to the optical link and the sensing and reference arms, thereby propagating the excitation pulse into the sensing arm and the at least one reference pulse into the reference arm.

18. The method of claim 17, wherein said propagating the at least one reference pulse in a reference arm comprises reflecting the at least one reference pulse.

19. The method of claim 17, wherein said propagating the at least one reference pulse in a reference arm comprises propagating the at least one reference pulse in an optical loop.

20. The method of claim 16, further comprising propagating the excitation pulse and the at least one reference pulse into an optical coupler connected to the optical link and the sensing and reference arms, thereby propagating at least a portion of the excitation pulse into the sensing arm and at least a portion of the at least one reference pulse into the reference arm.

* * * * *